United States Patent
Rona et al.

[11] Patent Number: 5,584,838
[45] Date of Patent: Dec. 17, 1996

[54] DISTAL TARGETING SYSTEM

[75] Inventors: Mehmet Rona, Cambridge; Douglas J. Ely, Chelsea, both of Mass.; James A. Evans, Portage, Mich.; Matthew S. Alves, Kalamazoo, Mich.; Lisa D. Sertic, Portage, Mich.; Christopher D. Philipp, Kalamazoo, Mich.

[73] Assignee: Stryker Corporation, Kalamazoo, Mich.

[21] Appl. No.: 203,664

[22] Filed: Feb. 28, 1994

Related U.S. Application Data

[63] Continuation of Ser. No. 839,671, Feb. 19, 1992, abandoned, which is a continuation-in-part of Ser. No. 727,652, Jul. 9, 1991, abandoned.

[51] Int. Cl.⁶ .......................... A61B 17/56; B23B 49/00; G01R 33/02
[52] U.S. Cl. .................. 606/96; 408/13; 408/16; 408/115 B; 408/97; 324/226
[58] Field of Search ................ 408/13, 16, 72 B, 408/115 B, 97; 606/172; 324/207.17, 207.18, 207.19, 243, 245, 246, 67, 326, 226

[56] References Cited

U.S. PATENT DOCUMENTS

| | | | |
|---|---|---|---|
| 837,133 | 3/1907 | Velasco | 606/172 |
| 2,844,977 | 7/1958 | Morse | 324/67 X |
| 3,062,076 | 11/1962 | Graig | 408/115 B X |
| 3,281,660 | 10/1966 | Studenick | 324/245 X |
| 3,282,132 | 11/1966 | Neuschotz | 408/115 B |
| 3,367,326 | 2/1968 | Frazier . | |
| 3,622,784 | 11/1971 | Guercio . | |
| 3,659,588 | 5/1972 | Kahn et al. . | |
| 3,683,354 | 8/1972 | Enk . | |
| 3,757,209 | 9/1973 | Schonstedt | 324/245 |
| 3,782,373 | 1/1974 | Smythe . | |
| 3,814,089 | 6/1974 | Deyerle . | |
| 3,836,848 | 9/1994 | Blevins | 324/67 |
| 3,882,287 | 5/1975 | Simmonds | 324/66 X |
| 4,173,228 | 11/1979 | Van Steenwyk et al. . | |
| 4,176,662 | 12/1979 | Frazer . | |
| 4,223,228 | 9/1980 | Kaplan | 324/207.2 X |
| 4,281,649 | 8/1981 | Derweduwen . | |
| 4,317,078 | 2/1982 | Weed et al. . | |
| 4,338,723 | 7/1982 | Benjamin . | |
| 4,386,532 | 6/1983 | Benjamin . | |
| 4,416,289 | 11/1983 | Bresler . | |
| 4,418,422 | 11/1983 | Richter et al. . | |
| 4,427,942 | 1/1984 | Sole | 324/67 X |
| 4,431,005 | 2/1984 | McCormick . | |
| 4,432,369 | 2/1984 | Halvorsen . | |
| 4,445,501 | 5/1984 | Bresler . | |

(List continued on next page.)

FOREIGN PATENT DOCUMENTS

| | | |
|---|---|---|
| 964149 | 3/1975 | Canada . |
| 091577 | 10/1983 | European Pat. Off. . |
| 320623 | 6/1989 | European Pat. Off. . |
| 2432173 | 1/1976 | Germany . |
| 1009445 | 4/1983 | U.S.S.R. . |

*Primary Examiner*—Robert A. Hafer
*Assistant Examiner*—Brian E. Hanlon
*Attorney, Agent, or Firm*—Flynn, Thiel, Boutell & Tanis, P.C.

[57] ABSTRACT

A femoral nail which can be implanted in a bone has a transverse hole, and an arrangement is provided for generating a magnetic field which has a maximum strength along an axis of the transverse hole and which decreases in strength in directions radially away from the axis. A drill guide for axially aligning a drill with the transverse hole has an axial drill opening through it, and first and second sensor arrangements are provided at axially spaced locations on the drill guide and each have a plurality of sensors which are at angularly spaced locations and are spaced radially from the opening through the drill guide. An arrangement responsive to the first and second sensor arrangements detects a deviation of the drill opening in the drill guide from coaxial alignment with the axis of the hole in the member, and provides an operator perceptible indication of a radial direction from the drill opening to the axis.

29 Claims, 21 Drawing Sheets

U.S. PATENT DOCUMENTS

| | | | |
|---|---|---|---|
| 4,517,540 | 5/1985 | McDougal | 336/206 |
| 4,526,177 | 7/1985 | Rudy et al. . | |
| 4,541,424 | 9/1985 | Grosse et al. . | |
| 4,545,106 | 10/1985 | Juengel . | |
| 4,572,198 | 2/1986 | Codrington . | |
| 4,621,628 | 11/1986 | Brudermann | 606/62 |
| 4,625,718 | 12/1986 | Olerud et al. . | |
| 4,654,589 | 3/1987 | Whethan et al. | 324/207.17 |
| 4,657,451 | 4/1987 | Tanaka | 324/207.17 X |
| 4,708,139 | 11/1987 | Dunbar, IV | 606/96 |
| 4,739,751 | 4/1988 | Sapega et al. | 606/96 |
| 4,779,319 | 10/1988 | Juengel . | |
| 4,781,181 | 11/1988 | Tanguy . | |
| 4,790,694 | 12/1988 | Wilent et al. . | |
| 4,800,873 | 1/1989 | Audell . | |
| 4,803,976 | 2/1989 | Frigg et al. . | |
| 4,846,162 | 7/1989 | Moehring . | |
| 4,850,344 | 7/1989 | Olerud et al. . | |
| 4,865,025 | 9/1989 | Buzzi et al. . | |
| 4,877,019 | 10/1989 | Vives . | |
| 4,905,698 | 3/1990 | Strohl, Jr. et al. . | |
| 4,943,770 | 7/1990 | Ashley-Rollman et al. | 324/207.17 |
| 4,969,889 | 11/1990 | Greig . | |
| 4,985,032 | 1/1991 | Goble | 606/96 |
| 4,998,058 | 3/1991 | Tofte et al. | 324/67 |
| 5,127,913 | 7/1992 | Thomas | 606/62 |
| 5,152,764 | 10/1992 | Goble | 606/96 |
| 5,178,621 | 1/1993 | Cook et al. | 606/96 |

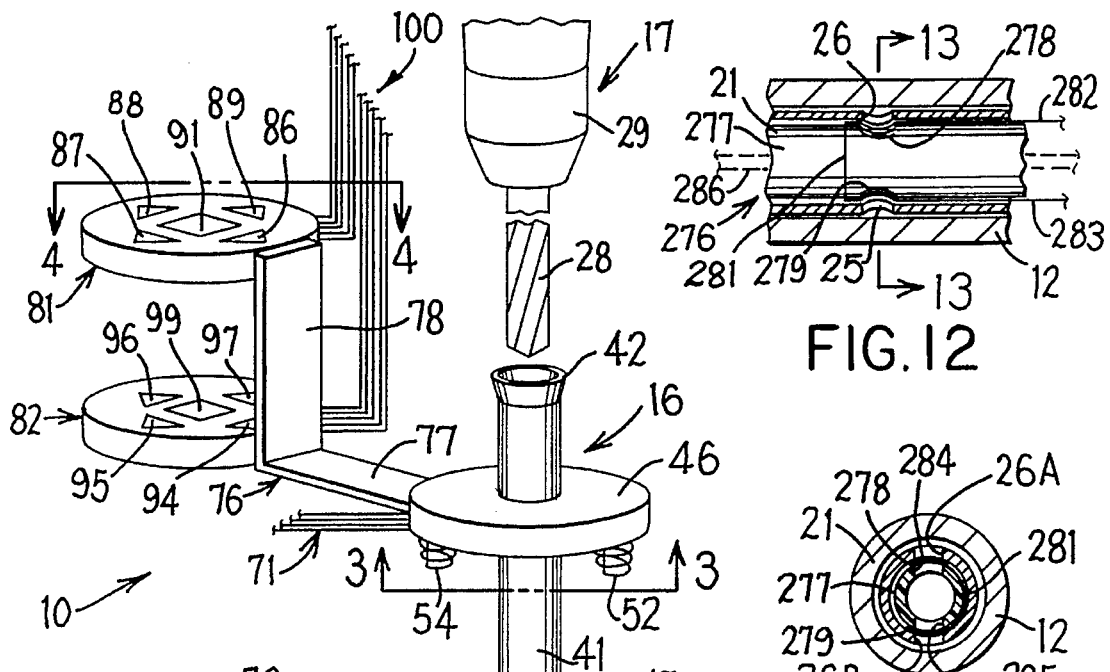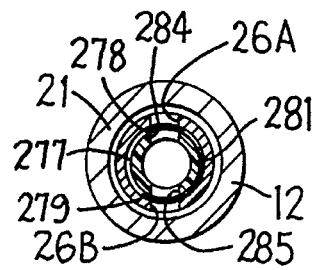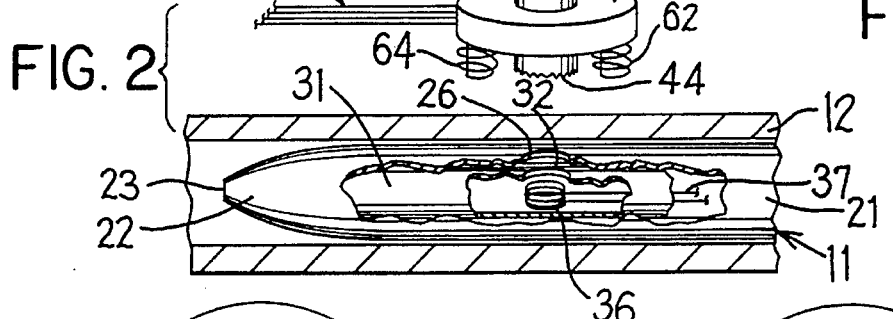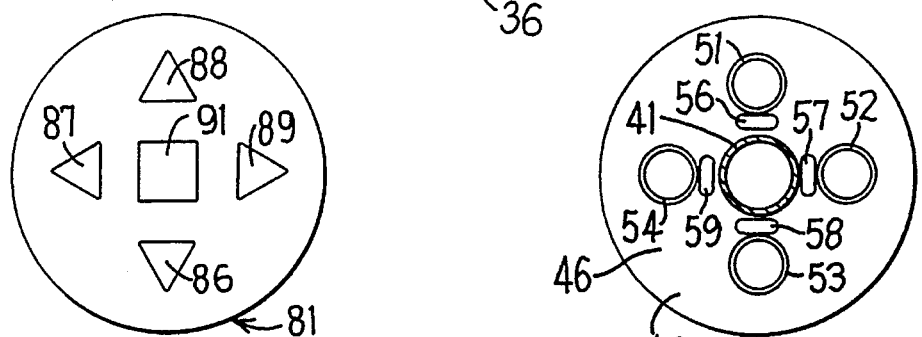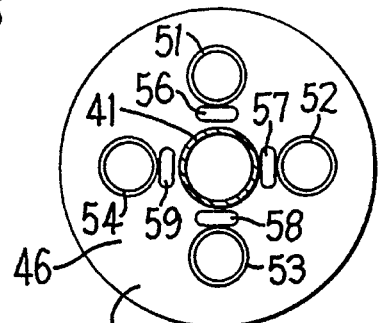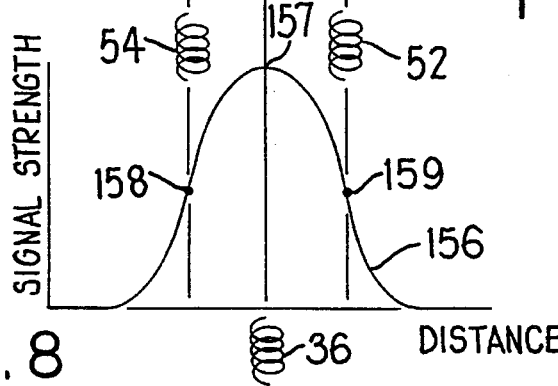

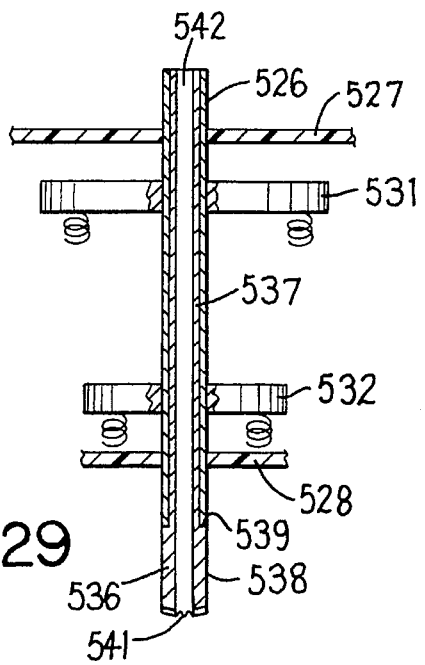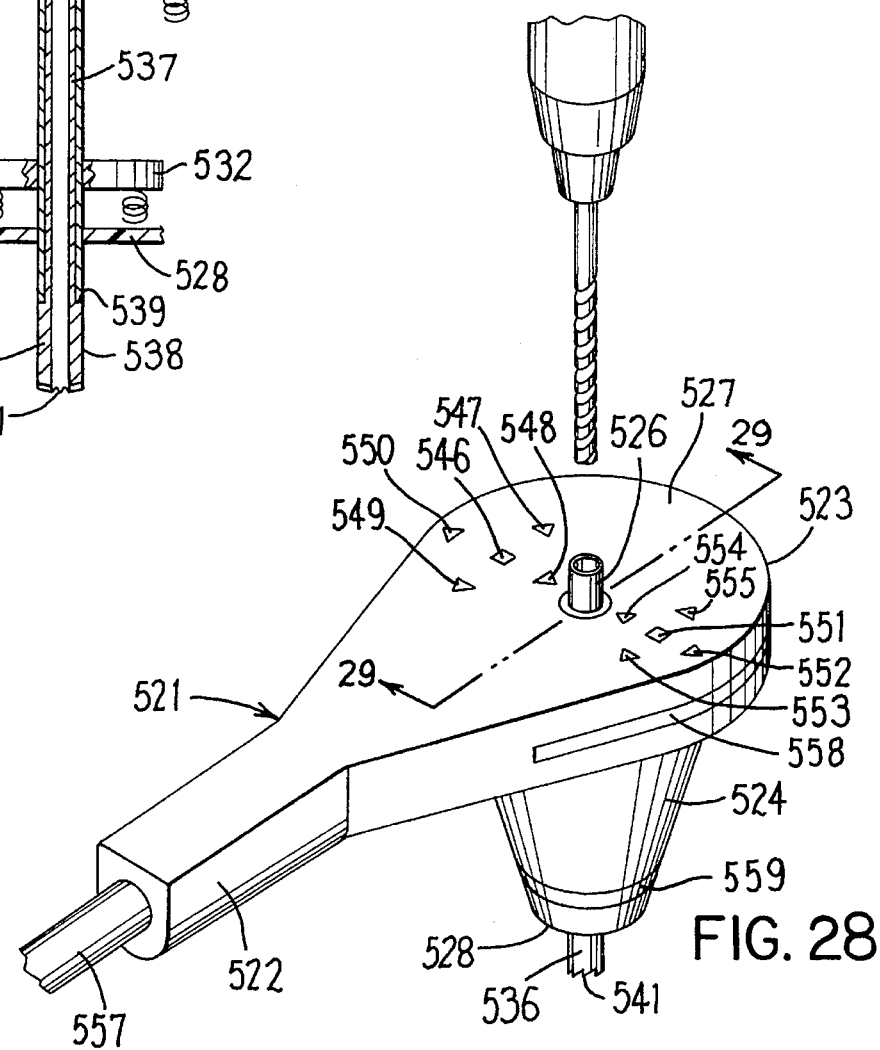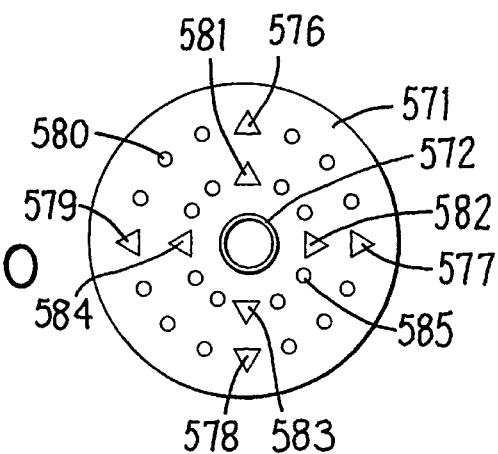

DISTAL TARGETING SYSTEM

This application is a continuation of U.S. Ser. No. 07/839,671 filed Feb. 19, 1992, now abandoned, which was in turn a continuation-in-part of U.S. Ser. No. 07/727,652 filed Jul. 9, 1991, now abandoned.

FIELD OF THE INVENTION

The present invention relates generally to a method and apparatus for effecting alignment of two components respectively disposed externally and internally of a body and, more particularly, to a method and apparatus for aligning a surgical drill guide with a transverse opening in a femoral nail implanted in a femur.

BACKGROUND OF THE INVENTION

In repairing broken bones, for example a broken femur, a common approach is to insert a tubular part called a femoral nail into the interior of the bone, and then secure it in place with one or more transversely extending screws. In order to achieve this result, a screw hole must be drilled in the bone in direct alignment with each transverse hole in the femoral nail after the femoral nail has been inserted in the bone. The drill should preferably pass cleanly through the transverse hole in the femoral nail, because otherwise it will produce metal chips and shavings from the femoral nail which may impede healing and may also be a source of future discomfort or pain for the patient. However, since the femoral nail is disposed inside the bone, is not possible to directly see the hole, and thus some arrangement must be provided to accurately align a surgical drill with the transverse hole through the femoral nail.

One approach has been to use X-rays to view the hole as the drill is being aligned with the hole and during the actual drilling, but this approach exposes the surgeon and other personnel to a certain degree of radiation for a relatively long period of time in comparison to that used for a standard X-ray photograph, which obviously presents health concerns.

Another traditional approach is to provide a magnetic source outside the body and a magnetic detector within the femoral nail at the transverse hole. The detector in the nail is coupled through wires to an indicator arrangement external to the patient, and the source of magnetism is moved until the detector indicates a maximum field, at which point it is assumed that the magnetic source is aligned with the opening in the nail. However, it is difficult to precisely detect the exact maximum of the field, because the field strength is relatively uniform in the general region of the maximum. Thus a certain amount of play or slop in the position of the magnetic source can occur without any significant variation in the field strength reading on the indicator arrangement, making accurate alignment difficult. Moreover, these arrangements typically ensure that drilling starts at a point which is approximately on the axis of the transverse hole through the nail, but do not ensure that the drill is properly axially aligned with both of the diametrically opposite openings defining the transverse hole along the full length of the drill so that the drill will pass cleanly through both openings in the nail with little or no direct contact with the nail.

Accordingly, an object of the present invention is to provide an arrangement capable of providing drill alignment which is substantially more accurate than that provided by known devices.

A further object is to provide an alignment arrangement which provides precise axial alignment of the entire length of the drill along the axis of the transverse hole.

A further object is to provide such an alignment arrangement which is easy to use.

SUMMARY OF THE INVENTION

The objects and purposes of the invention, including those set forth above, are met by providing an apparatus which includes an arrangement for generating a magnetic field changing in strength in directions radially away from an axis, a sensor arrangement for measuring the strength of the magnetic field at a plurality of locations spaced radially from and angularly about an elongate part, and an arrangement responsive to the sensor arrangement for detecting a radial deviation of the elongate part from alignment with the axis and for providing an operator perceptible indication of a radial direction from the part to the axis.

In a different form of the invention, an apparatus for axially aligning a drill with a transverse hole in a member disposed in a body includes an arrangement in the member for generating a magnetic field which has a maximum strength along an axis of the transverse hole and which decreases in strength in directions radially away from the axis, a drill guide having an axial drill opening therethrough, first and second sensor arrangements provided at axially spaced locations on the drill guide and each having a plurality of sensors which are at angularly spaced locations and are spaced radially from the opening through the drill guide, and an arrangement responsive to the first and second sensor arrangements for detecting a deviation of the drill opening in the drill guide from coaxial alignment with the axis of the hole in the member, and for providing an operator perceptible indication of a radial direction from the drill opening to the axis.

A further form of the present invention is a method which involves the steps of generating a magnetic field changing in strength in directions radially away from an axis, comparing the magnetic field strengths at a plurality of locations spaced radially from and angularly about an elongate part to detect a radial deviation of the elongate part from alignment with the axis, and providing an operator perceptible indication of a radial direction from the part to the axis.

Yet another form of the invention involves an apparatus which includes a member having a first arrangement defining an axis, and a second arrangement for positioning an elongate part to extend along the axis, the second arrangement including a third arrangement on the member for generating a magnetic field, a sensor arrangement for measuring the strength of the magnetic field in the region of the elongate part, and a fourth arrangement responsive to the sensor arrangement for detecting radial deviation of the elongate part in excess of a radial deviation limit from alignment with the axis and for providing an operator perceptible indication of a radial direction from the part to the axis, wherein the fourth arrangement includes a variable gain amplifier arrangement for amplifying signals from the sensor arrangement, and an arrangement for respectively increasing and decreasing the gain of the amplifier arrangement when an output signal from the amplifier arrangement is respectively below and above respective predetermined magnitudes.

BRIEF DESCRIPTION OF DRAWINGS

Preferred embodiments of the present invention are described in more detail below with reference to the accompanying drawings, in which:

3

Figure 1:
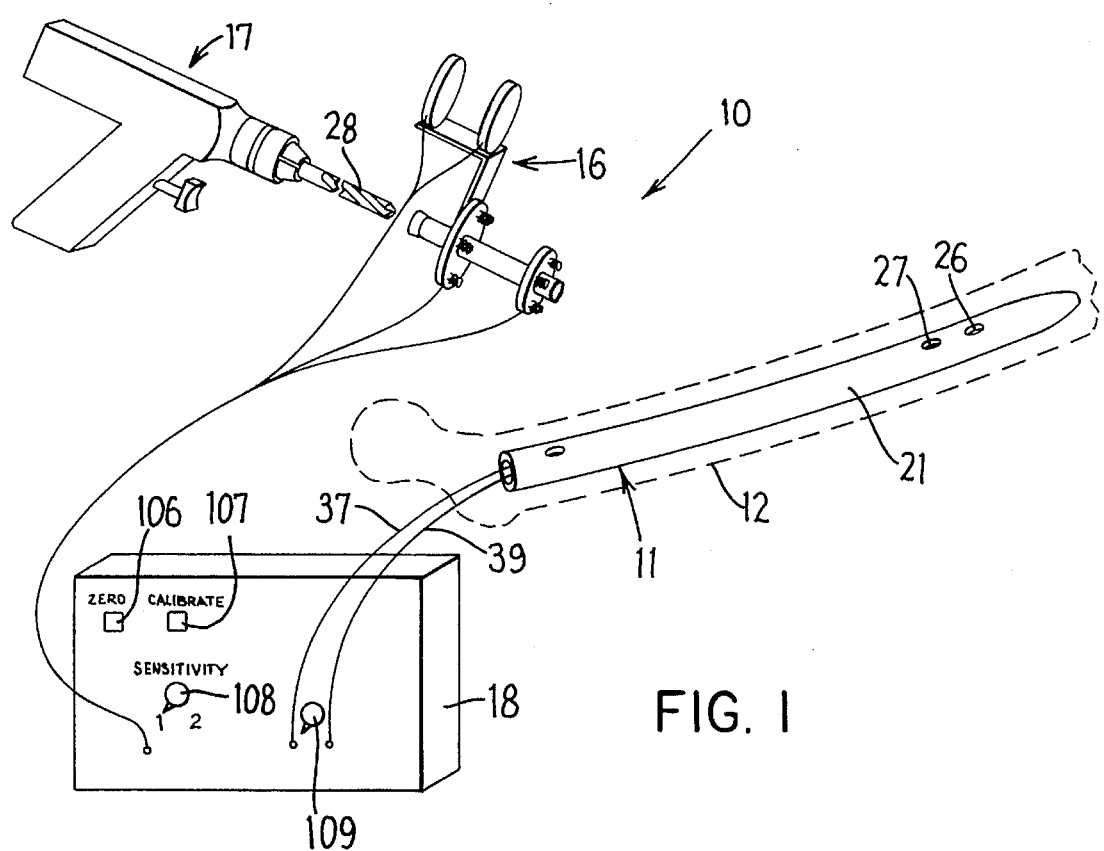
Figure 5:
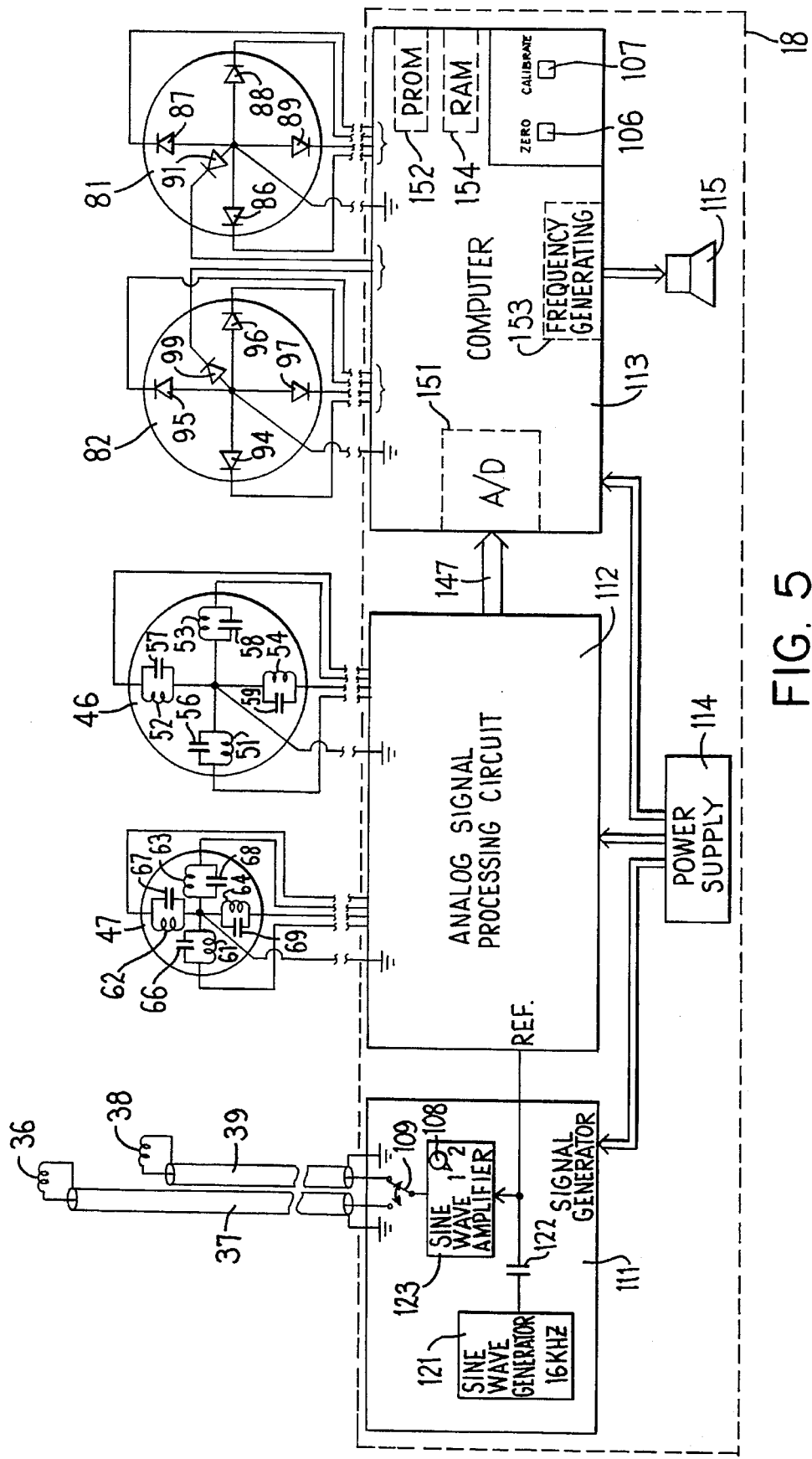
Figure 6:
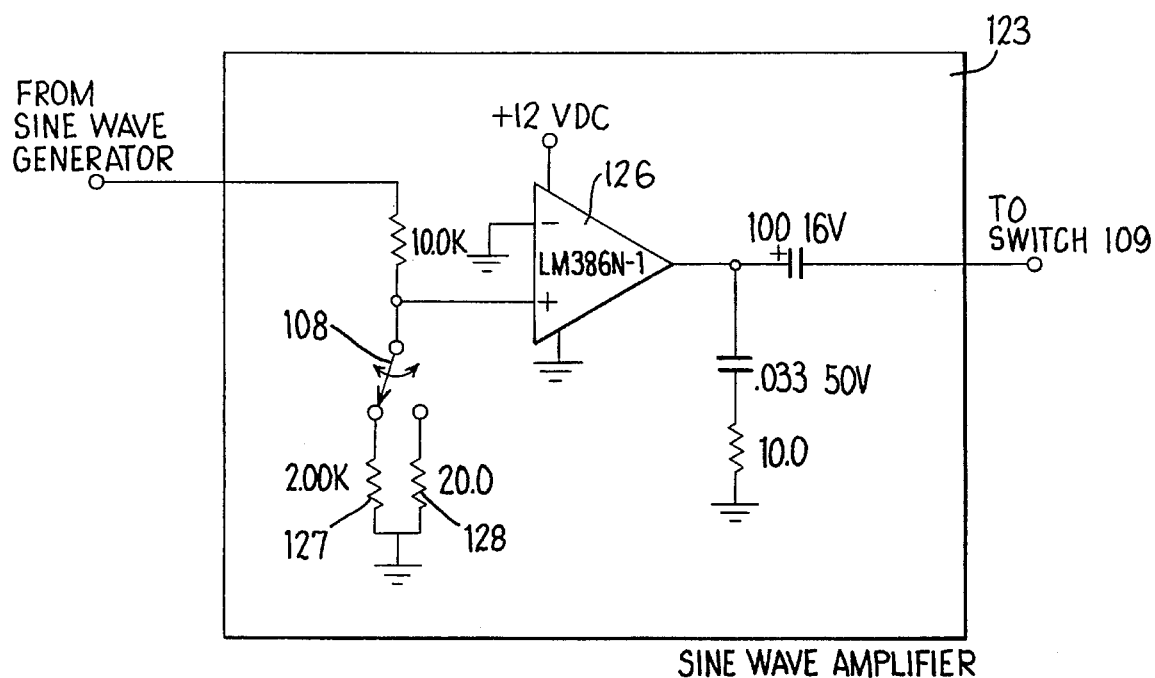
Figure 7:
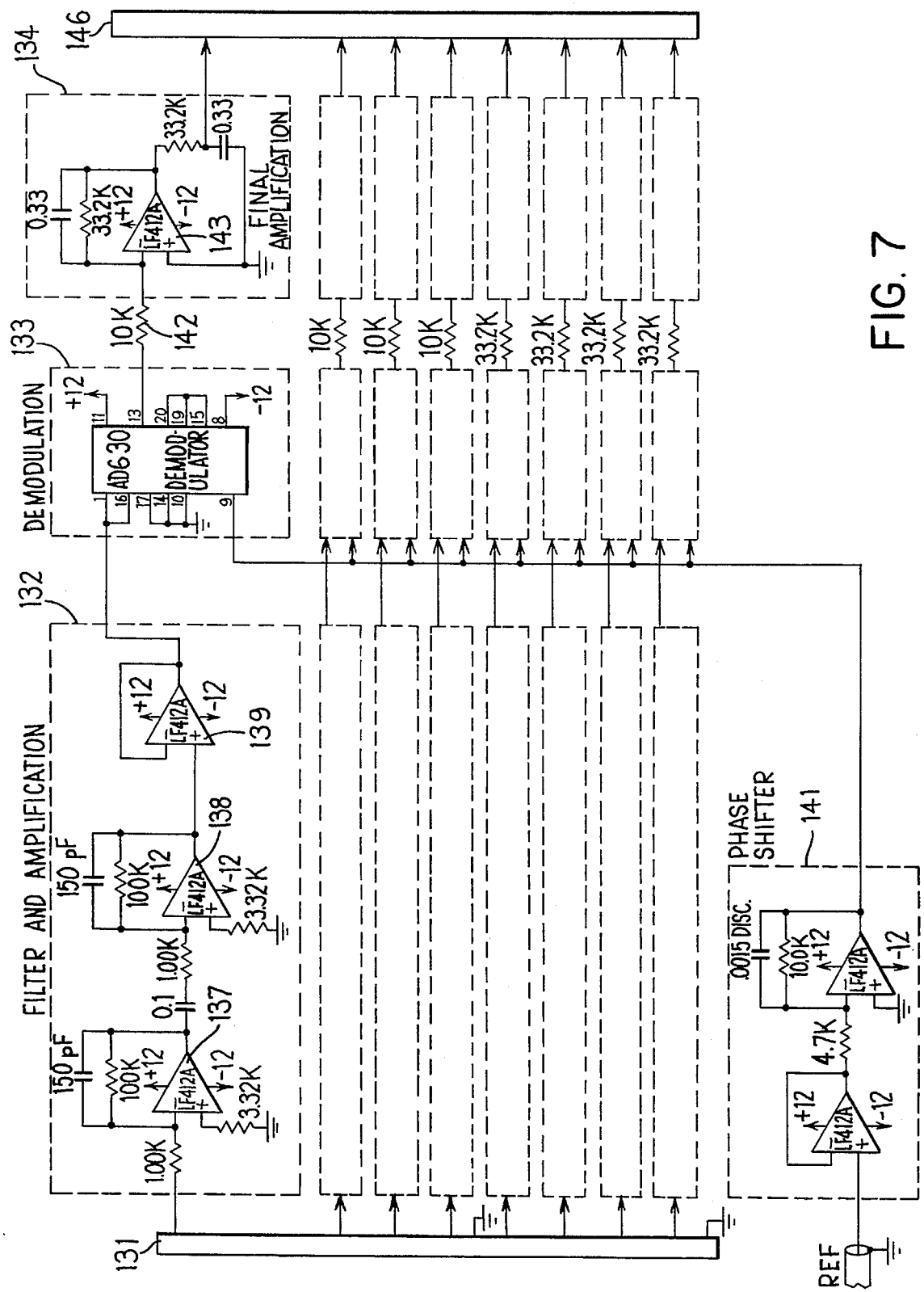
Figure 9:
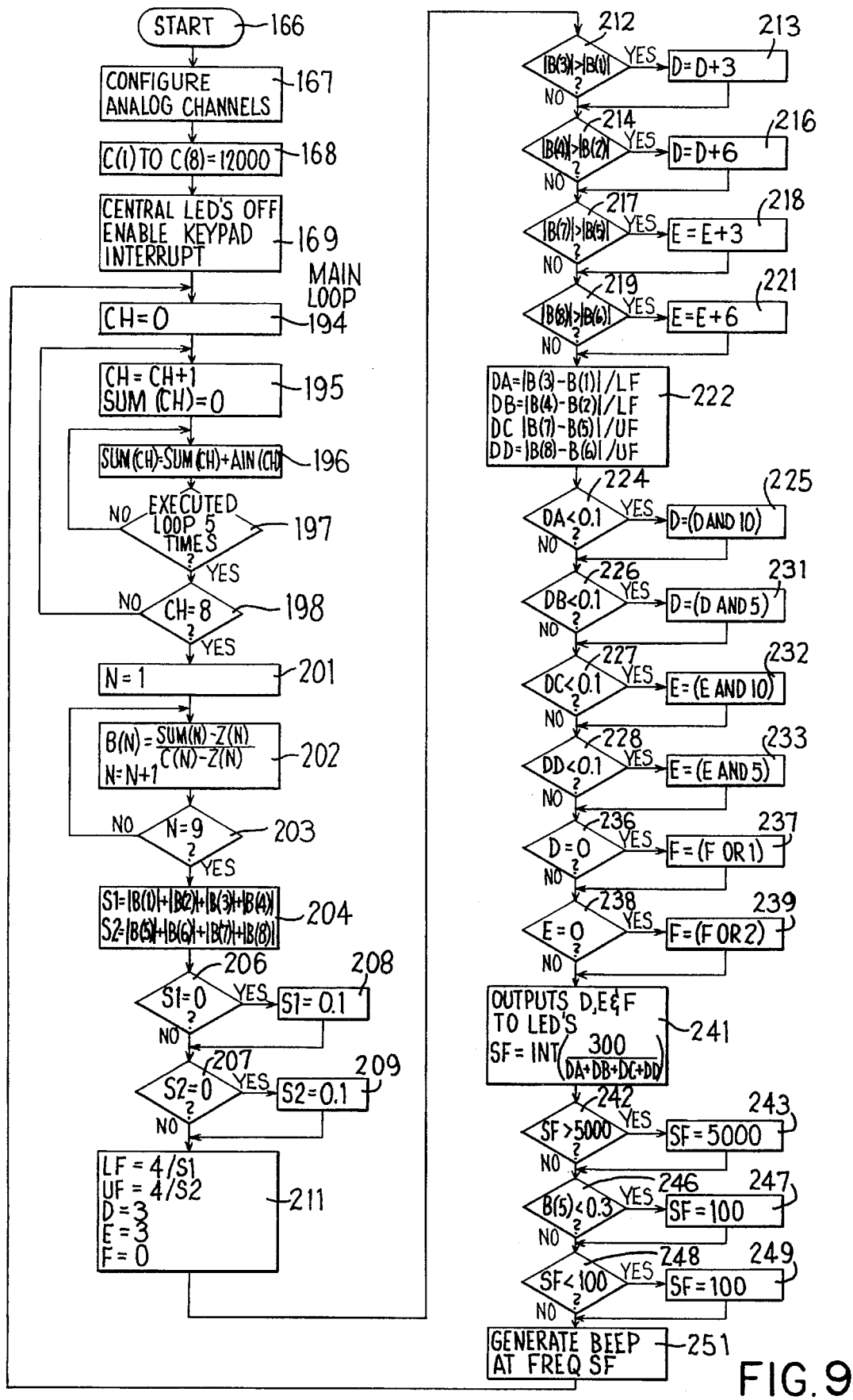
Figure 10:
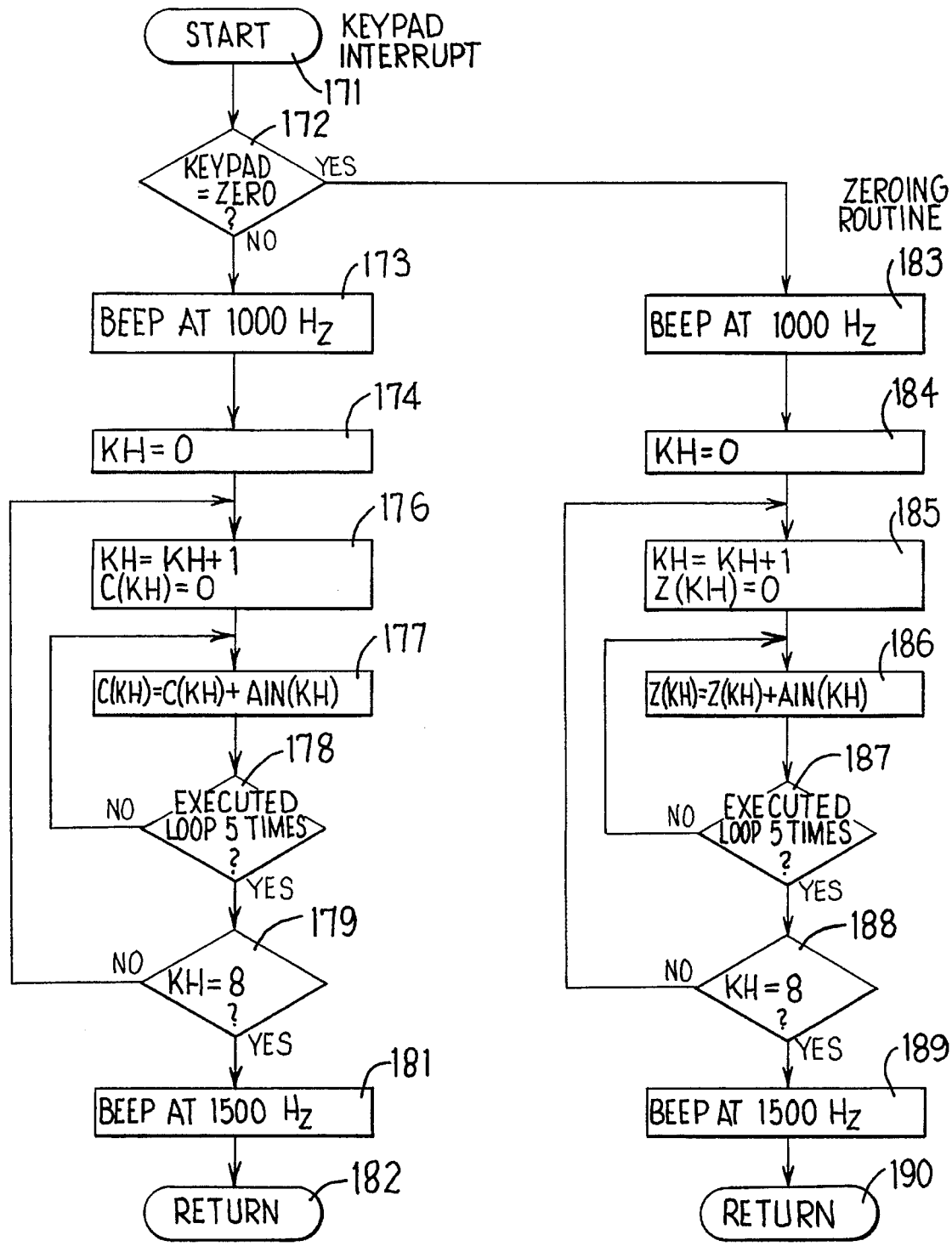
Figure 11:
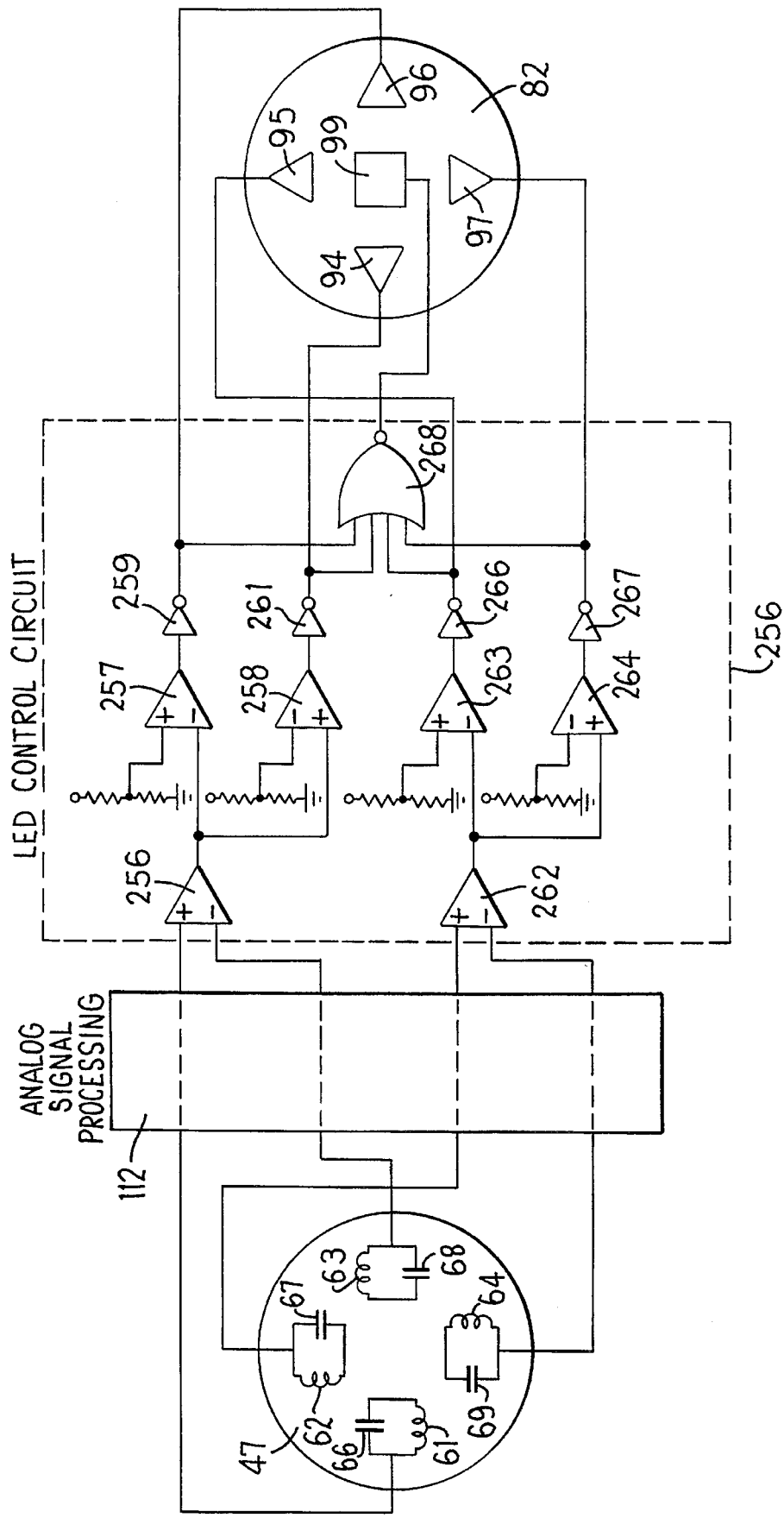
Figure 14:
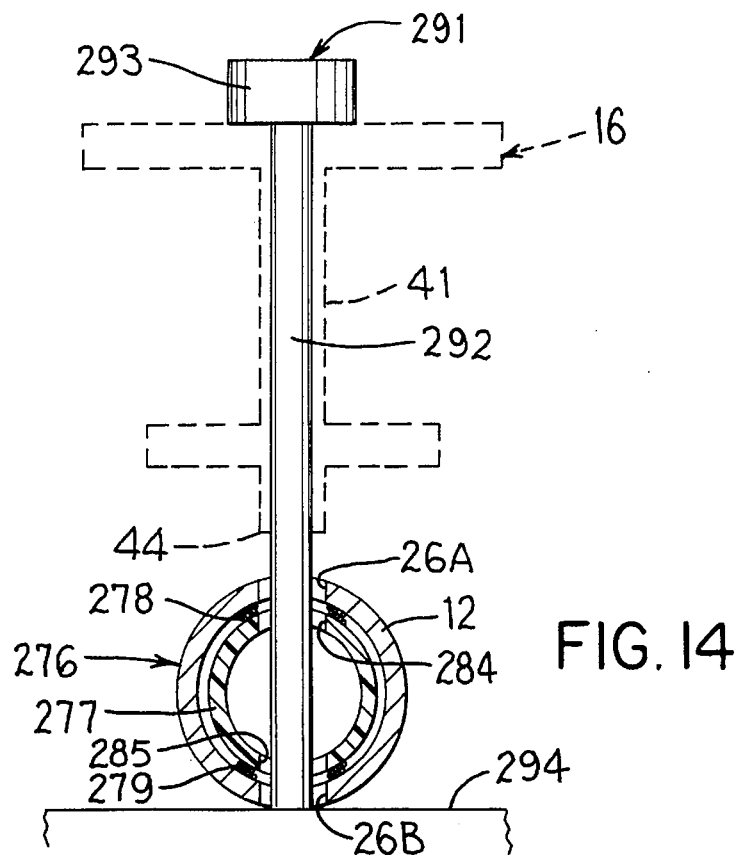
Figure 15:
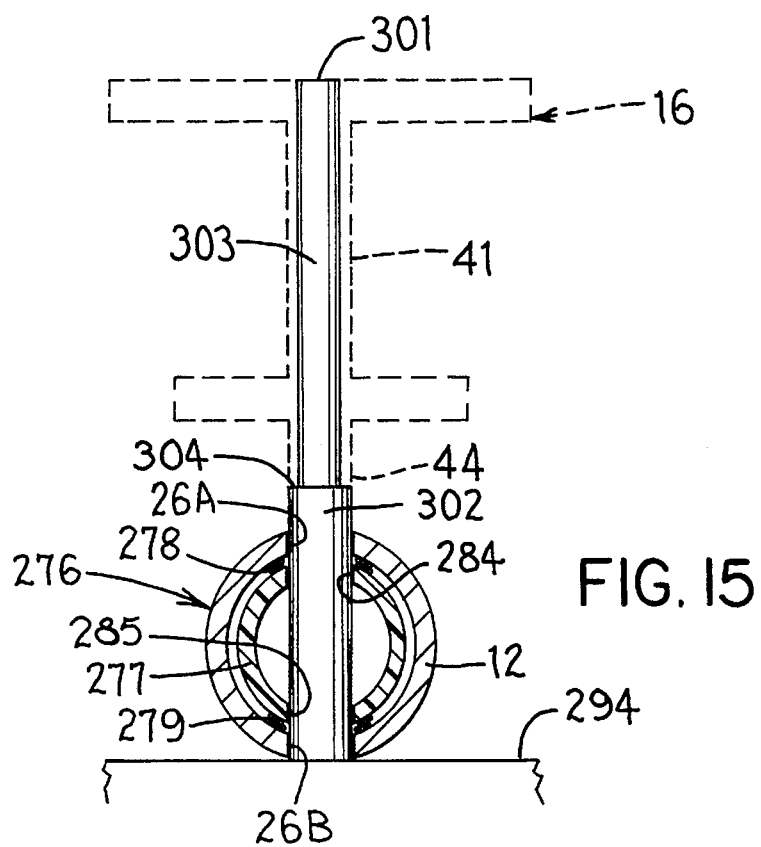
Figure 16:
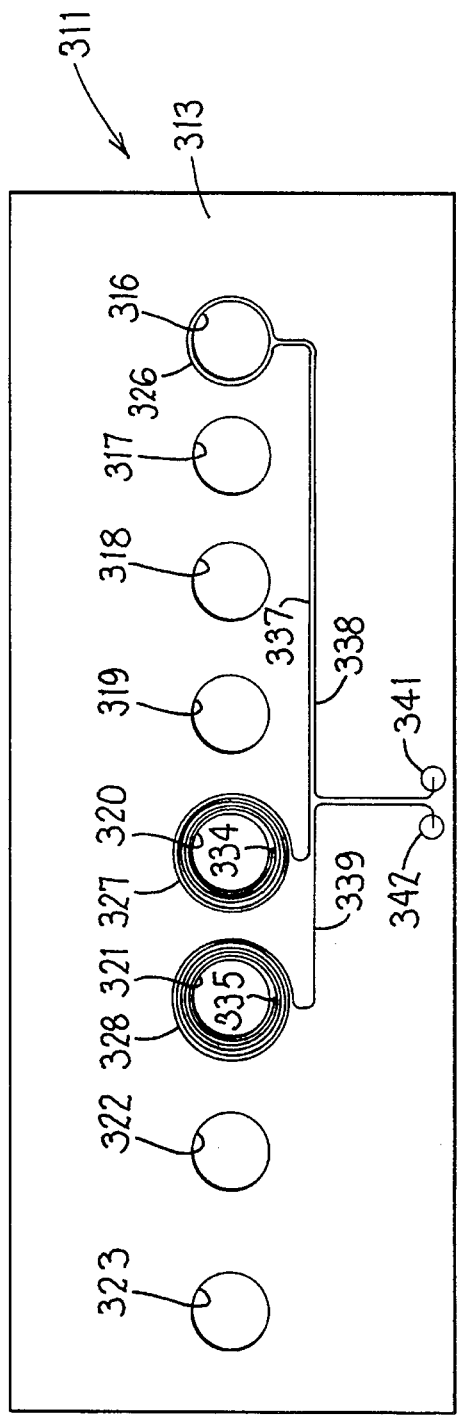
Figure 17:
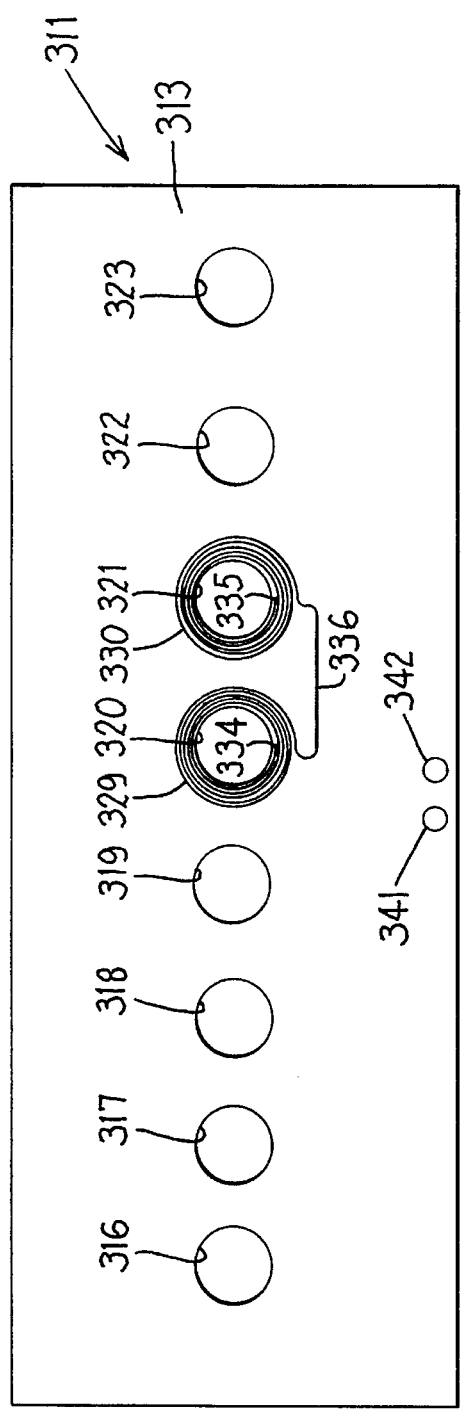
Figure 18:
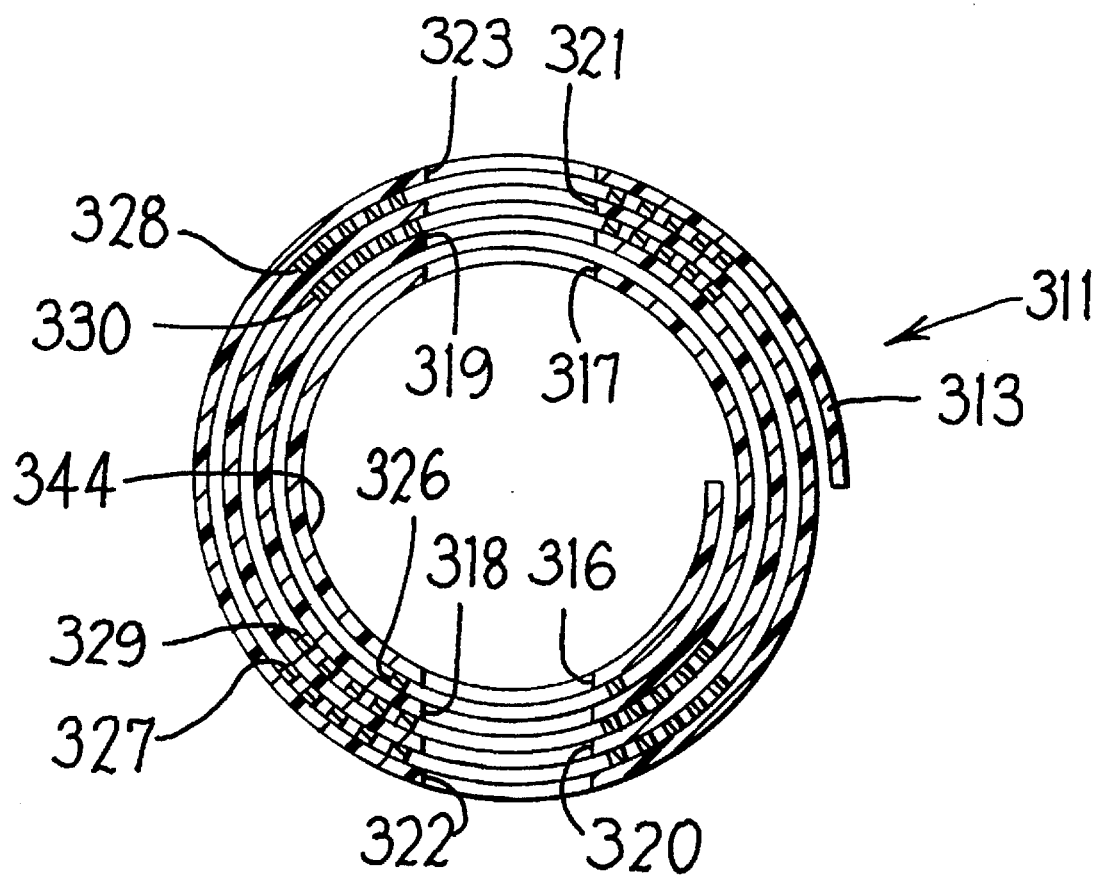
Figure 19:
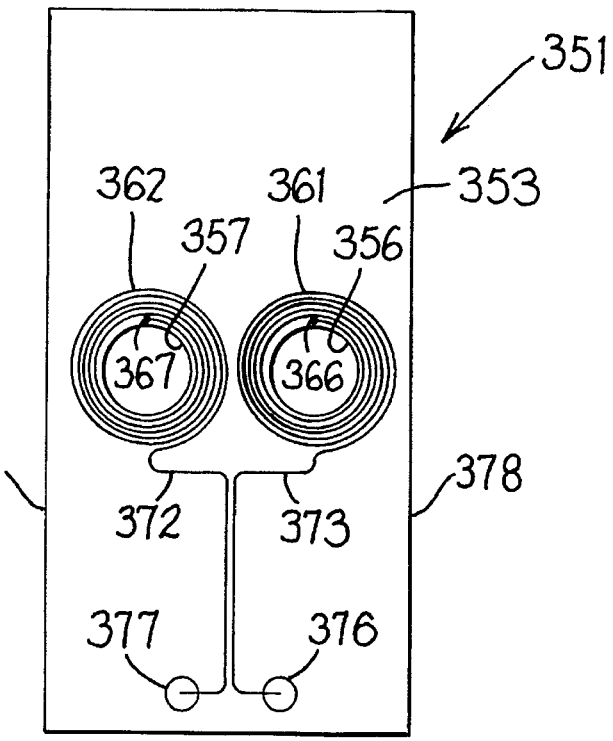
Figure 20:
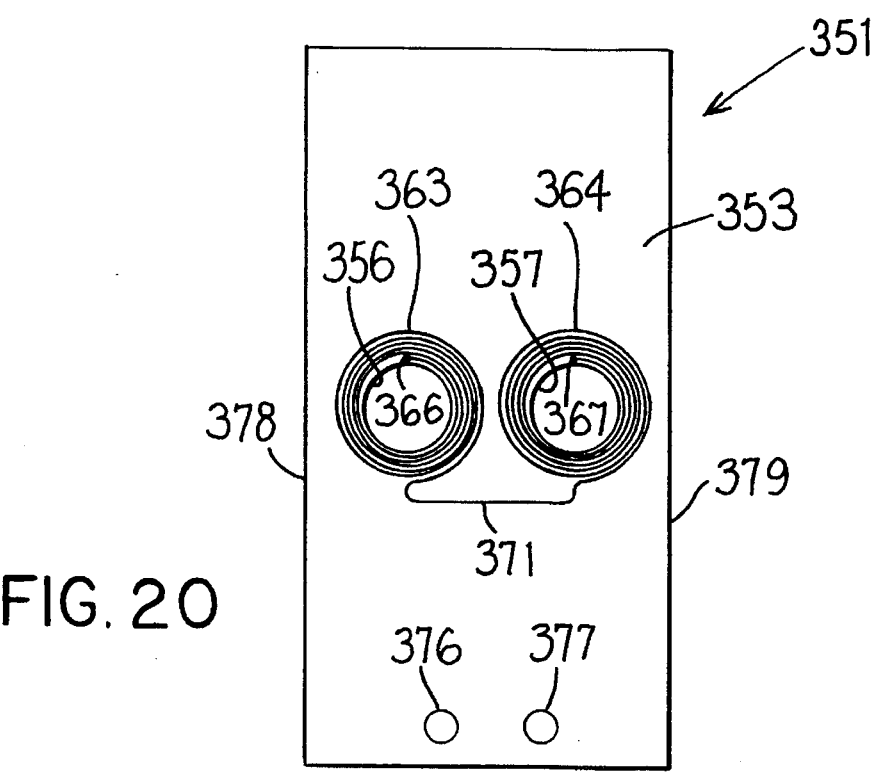
Figure 21:
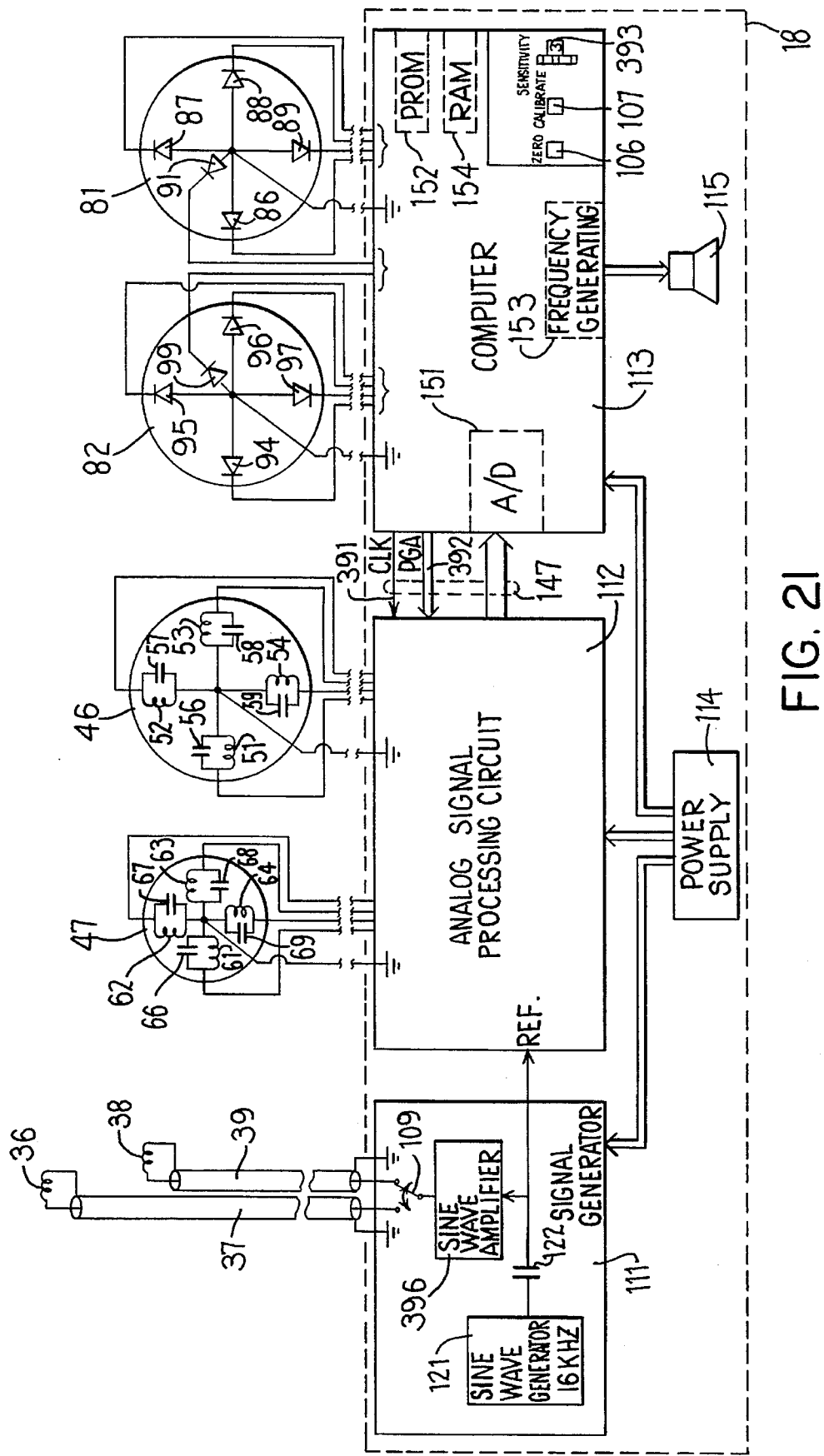
Figure 23:
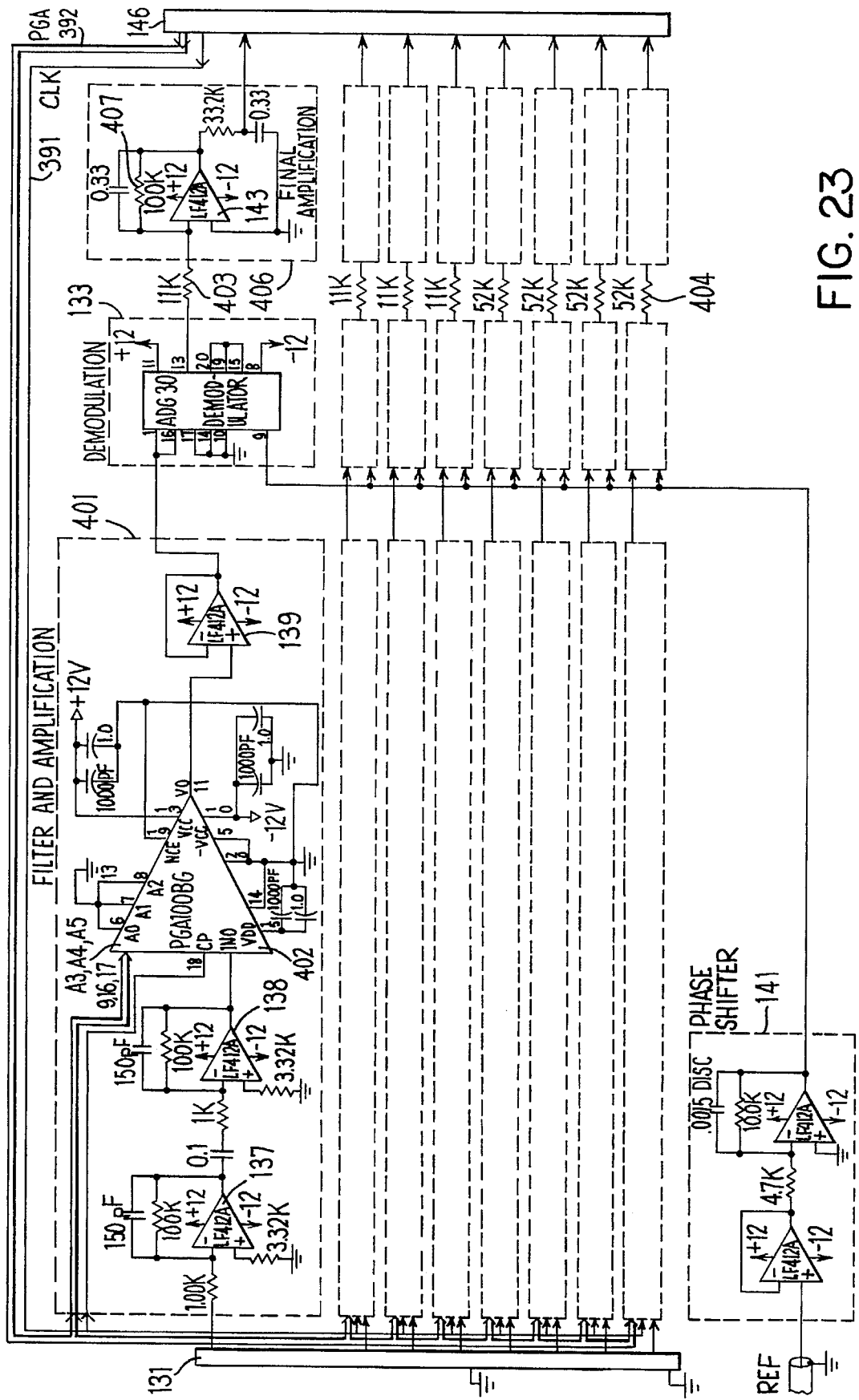
Figure 31:
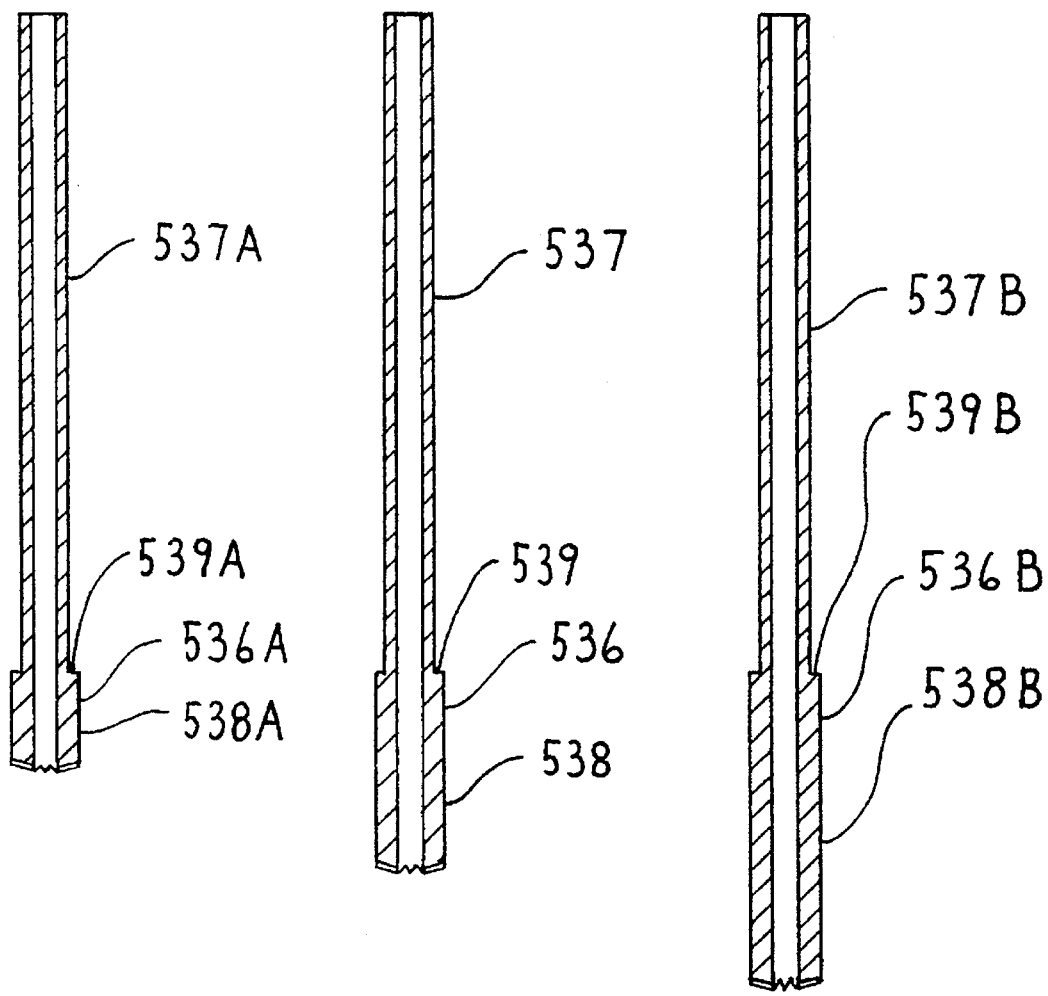

FIG. 1 is a diagrammatic view of a surgical drill alignment system embodying the present invention;

FIG. 2 is a fragmentary side view of certain components of the system of FIG. 1, including a drill guide, part of a surgical drill, and a femoral nail assembly disposed in a femur and shown in section;

FIG. 3 is a view taken along the line 3—3 in FIG. 2;

FIG. 4 is a view taken along the line 4—4 in FIG. 2;

FIG. 5 is a block diagram of an electrical circuit of the system of FIG. 1;

FIG. 6 is an electrical schematic diagram of a component of the diagram of FIG. 5;

FIG. 7 is an electrical schematic diagram of another component of the diagram of FIG. 5;

FIG. 8 s a graph showing variation of with radial distance of the strength of a magnetic field in the embodiment of FIG. 1;

FIGS. 9 and 10 are flowcharts of a program executed by a computer which is part of the circuit of FIG. 5;

FIG. 11 is a diagrammatic view of an alternative embodiment of a portion of the arrangement shown in FIG. 5;

FIG. 12 is a fragmentary sectional side view of an alternative embodiment of the femoral nail assembly shown in FIG. 2;

FIG. 13 is a sectional view taken along the line 13—13 in FIG. 12;

FIG. 14 is an end view, partly in section, of an alignment part with the femoral nail assembly of FIG. 12 and the drill guide of FIG. 2;

FIG. 15 is a view similar to FIG. 13 but showing an alternative embodiment of the alignment part;

FIG. 16 is an elevational view of a front side of an emitter unit which is an alternative embodiment of a coil present in the system of FIGS. 1 and 2;

FIG. 17 is an elevational view of the rear side of the emitter unit of FIG. 16;

FIG. 18 is a sectional view of the emitter unit of FIG. 16 after being rolled into a normal operational configuration;

FIGS. 19 and 20 are elevational views of the front and rear sides of an emitter unit which is an alternative embodiment of the emitter unit of FIGS. 16 and 17;

FIG. 21 is a block diagram similar to FIG. 5 of an alternative embodiment of an electrical circuit for the system of FIG. 1;

FIG. 21 is an electrical schematic diagram of a component of the diagram of FIG. 21;

FIG. 23 is an electrical schematic diagram of another component of the diagram of FIG. 21;

FIGS. 24–27 are flowcharts of a program executed by a computer which is part of the circuit of FIG. 21;

FIG. 28 is a perspective view of an alternative embodiment of a guide device which is a component of the system of FIG. 1;

FIG. 29 is a sectional view taken along the line 29—29 in FIG. 28;

FIG. 30 is a top view of part of a further alternative embodiment of the guide device; and FIG. 31 is a side view of a set of interchangeable guide tubes, each of which can be used as a component of the embodiment of FIGS. 28 and 29.

4

DETAILED DESCRIPTION

FIG. 1 is a diagrammatic view of a distal targeting system 10 embodying the present invention. The targeting system 10 includes a nail assembly 11 which has been inserted into a broken femur bone 12, a drill guide device 16, a conventional surgical drill 17, and an electronic control unit 18. The guide device 16 and nail assembly 11 are shown in more detail in FIG. 2.

Referring to FIG. 2, the nail assembly 11 includes a femoral nail 21, which is a metal tube having at a distal end thereof a tapered end portion 22, and having at the outer end of the tapered portion a circular end hole 23. The femoral nail has in diametrically opposite sides thereof aligned circular openings 26A and 26B which together define a transverse hole 26 through the femoral nail. As shown in FIG. 1, the femoral nail 21 has a short axial distance from the transverse hole 26 a similar transverse hole 27.

The femoral nail 21 is itself conventional and, in a conventional manner, is to be permanently secured in the bone 12 by two conventional and not-illustrated screws which each extend through a respective one of the openings 26 and 27 and through a respective transverse hole drilled through the bone 12 in alignment with hole 26 or 27. The focus of the present invention is drilling of the holes through the bone 12 in precise and accurate alignment with the holes 26 and 27 in the nail 21. The holes are drilled in the bone 12 with the nail 21 in place, and it is thus important that the drill pass though each of the openings 26 and 27 in the nail so as to have little or no contact with the nail itself, so that the drill does not shave from the nail small pieces of metal which may impede the healing process and may produce future pain or discomfort for the patient. The drill guide device 16 and control unit 18 according to the invention have therefore been developed to ensure that the drill bit 28 mounted in the chuck 29 (FIG. 2) of the drill 17 is precisely aligned with one of the openings 26 or 27 in the nail 21 as it is used to drill the associated transverse opening through the bone.

According to the preferred embodiment of the invention, the nail assembly 11 includes an elongate plastic sleeve 31 (FIG. 2) which is removably inserted in the femoral nail 21 and has in it a pair of aligned transverse openings defining a transverse hole 32 which is precisely coaxially aligned with the transverse hole 26. The tube has a similar, not-illustrated transverse hole aligned with the transverse hole 27 in the nail 21. An emitter coil 36 is fixedly supported within the sleeve 31 so as to be precisely coaxially aligned with the transverse holes 26 and 32 in the nail 21 and sleeve 31. The coil is connected by leads 37 to the control unit 18. A similar emitter coil 38 (FIG. 5) is provided in the sleeve 31 in precise coaxial alignment with the hole 27, and is connected at 39 to the control unit 18.

The guide device 16 includes a cylindrical guide tube 41 which is flared at its upper end 42 so as to facilitate easy insertion therein of the drill bit 28 of drill 17. At the opposite end, the tube 41 is provided with a plurality of circumferentially spaced teeth 44, which can be driven into the material of the bone 12 by striking the end 42 of the guide tube 41 with a small hammer after the guide device 16 has been properly oriented with the respect to the bone, in order to help hold the guide device 16 in that orientation.

The guide tube 41 has concentrically fixedly mounted on it an upper disk 46 and a lower disk 47, which in the preferred embodiment are circular printed circuit boards. The upper disk 46 has a larger diameter than the lower disk 47.

With reference to FIGS. 2 and 3, the upper disk 46 has mounted on its lower side four Upper detecting or sensor coils 51–54 which are each spaced radially outwardly the same distance from the guide tube 41 and are provided at equal angular intervals of 90° about the guide tube 41. Each of the upper detecting coils 51–54 is oriented so that its axis extends parallel to the axis of the guide tube 41, and is a 1000 μH surface mount ferrite core inductor available from Toko America as type 43FS. Also mounted on the upper disk 46 adjacent each of the coils 51–54 is a respective conventional 0.1 μF monolithic ceramic capacitor 56–59 connected in parallel with the adjacent coil. In a similar manner, the lower disk has mounted thereon four lower detecting or sensor coils 61–64 and four associated capacitors 66–69. The upper detecting coils 51–54 are coupled by a respective group of leads 71 to the control unit 18 of FIG. 1, and the lower detecting coils 61–64 are connected by a further group of leads 72 to the control unit 18.

An L-shaped metal bracket 76 has two legs 77 and 78, the end of leg 77 being fixedly secured to the upper disk 46 so t, hat leg 77 extends directly radially outwardly from upper disk 46, and the leg 78 being oriented to extend upwardly from the leg 77 parallel to the axis of the guide tube 41. Fixedly mounted to the upper and lower ends of the leg 78 are respective vertically spaced, disk-like light emitting diode (LED) displays 81 and 82, which are of substantially of the same size and are coaxial about an axis extending parallel to the axis of the guide tube 41. As shown in FIG. 4, the upper LED display 81 includes four LEDs of triangular shape which serve as directional arrows and are each spaced radially outwardly from a single square center LED 91, the triangular LEDs being provided at equal angular intervals of 90° about the center LED 91 and each being oriented to point radially outwardly in a direction away from the center LED 91. The LEDs 86–89 and 91 are all embedded in a disk-shaped plastic or synthetic resin material with their upper surfaces approximately flush with the upper surface of the plastic or resin material. The LEDs 86–89 and 91 are all electrically driven by the control unit 18 through a group of leads 92, and are all conventional and commercially available parts, the LEDs 86–89 being available from Panasonic Industrial Sales, Secaucus, N.J. Jersey, as part number LN312GP, and the LED 91 being available from the same source as part number LN350GP. In a similar manner, the lower LED display 82 includes four triangular or arrow-shaped LEDs 94–97 and a square center LED 99 arranged in a similar pattern and driven through an associated group of leads 100 by the control unit 18.

In FIG. 1, the control unit 18 has manually operable ZERO and CALIBRATE buttons 106 and 107, which are each a momentary push button switch. Further, a SENSITIVITY switch 108 can be set to a selected one of two positions, and an emitter coil select switch 109 can be set to one of two positions in which it respectively selects one of the emitter coils 36 and 38 disposed in the femoral nail 21.

A block diagram of the control unit 18 is shown in FIG. 5, and includes a signal generator portion 111, an analog signal processing circuit 112, a computer 113, a power supply 114 which supplies power to the entire system, and a speaker 115.

The signal generator 111 includes a conventional sine wave generator circuit 121, which outputs a sine wave signal at a frequency of substantially 16 KHz. The output of the sine wave generator 121 is coupled through an AC coupling capacitor 122 to a reference input of the analog signal processing circuit 112, and to an input of a sine wave amplifier 123 which includes the SENSITIVITY switch 108. The output of the sine wave amplifier circuit 123 can be selectively coupled through the switch 109 to one of two coaxial cables 37 and 39, which are each approximately five feet long and serve as leads for the respective emitter coils 36 and 38. The emitter coils 36 and 38 in the preferred embodiment are 1,000 μH inductors, and as a result of the AC signal supplied to the selected coil 36 or 38, the selected coil emits a 16 KHz alternating magnetic field, in particular an oscillating magnetic field with an axial component which changes in strength.

The specific circuitry within the sine wave amplifier 123 of FIG. 5 is shown in more detail in FIG. 6, and includes an audio amplifier 126 which is a conventional and commercially available LM386N-1 integrated circuit available from National Semiconductor Corporation, Santa Clara, Calif. Moving the SENSITIVITY switch 108 between its two positions causes a selected one of two resistors 127 and 128 to be coupled into the circuit, the resistors 127 and 128 having different values and thus causing the sine wave amplifier circuit 123 to have one of two different gains, which in turn affects the magnitude of the AC signal supplied to the selected emitter coil and thus the strength of the magnetic field issued by that emitter coil.

In FIG. 5, each 0.1 μF capacitor 56–59 and 66–69 and the associated coil 51–54 or 61–64 form a resonant or "tank" circuit with a resonant frequency of 16 KHz. When the detecting coils are within the magnetic field produced by the selected emitter coil, the alternating magnetic field induces a 16 KHz signal in each of the detecting coils, which signals are supplied to the analog signal processing circuit 112.

The analog signal processing circuit 112 of the preferred embodiment is shown in more detail in FIG. 7, and includes a connector 131 through which are received the eight signals from the respective detecting coils. The respective circuit arrangements used to process these signals from each of the eight detecting coils are effectively identical, and thus only one of the circuit arrangements is shown in detail in FIG. 7.

In particular, each signal passes through a filtering and amplification circuit 132, then a demodulation circuit 133, and then a final filtering and amplification circuit 134. The input signal to the filtering and amplification circuit 132 is supplied to an inverting operational amplifier 137 which is a conventional LF412A component commercially available from National Semiconductor Corporation, and which has a gain of 100. The 150 pF capacitor in the feedback network provides single pole (−6 db/octave) low pass filtering with a corner frequency of approximately 67 KHz. The output of this amplifier is AC coupled to the input of a second inverting operational amplifier 138, which also has a gain of 100 and adds an additional pole of low pass filtering. The output of this amplifier is supplied to the input of a third operational amplifier which is arranged as a voltage follower, and which serves to buffer the signal being supplied to the demodulation circuit 133.

The demodulation circuit 133 includes an AD630 demodulator, which is a conventional integrated circuit commercially available from Analog Devices, Inc., Norwood, Mass., and which is configured as a synchronous detector. More specifically, the output at pin 13 is proportional to the amplitude of the component of the input signal which has the same frequency and phase as a reference signal supplied from the sine wave generator 121 (FIG. 5) through capacitor 122 and a phase shifter circuit 141 (FIG. 7). The phase shifter circuit 141 supplies the same reference signal to each of the demodulation circuits 133. The output at pin 13 of the AD630 can go positive or negative, depending on whether the input signal is in phase with or 180° out of phase with the reference signal. The output of the demodulation circuit 133 is supplied through a 10K resistor 142 to the final amplification circuit 134, where operational amplifier 143 and associated components serve as a two-pole (−12 db/octave) low pass filter with a corner frequency of approximately 100 Hz. It also serves as a final amplification stage.

The resistor 142 has a value of 10K for the signals from only four of the detector coils, and has a value of 33.2K for the signals from the other four detector coils. This is because, as evident from FIG. 2, the emitter coil 36 generating the magnetic field is closer to the four detector coils on lower disk 47 than to the four detector coils on upper disk 46, and thus the different values used for the resistor 142 adjust the gain of the associated final amplification circuit 134 in an appropriate manner so as to ensure the outputs of all eight final amplification circuits 134 are effectively normalized with respect to each other.

The 150 pF capacitors in the filtering and amplification circuits 132 introduce some phase shift into the respective signals passing though those circuits. Since the two input signal to each demodulation circuit 133 must ideally be either in phase or 180° out of phase, the phase shifter circuit 141 is provided simply to introduce into the 16 KHz reference signal received from the sine wave generator a phase shift corresponding to that generated by each filtering and amplification circuit 132.

The output signals from all eight final amplification circuits 134 are supplied through a connector 146 and a cable 147 (FIG. 5) to the computer 113.

In the preferred embodiment, the computer 113 is a conventional and commercially available single-board computer, a variety of which are readily available from a number of manufacturers. In the preferred embodiment, the single board computer is commercially available from Octagon Systems of Westminster, Colo. as model number SBS2300H. The computer 113 includes an analog-to-digital (A/D) converter 151 which receives the signals on cable 147 from the analog signal processing circuit 112, a programmable read only memory (PROM) which stores the program executed by the computer, and a random access memory (RAM) 154 where the program can store variable values and other information. The program stored in the PROM 152 in the preferred embodiment will be described in detail later. The computer 113 has an input port to which are connected the outputs of the ZERO and CALIBRATE switches 106 and 107, and has output ports which are used to control the LEDs 86–89, 91, 94–97 and 99 on the upper and lower display disks 81 and 82. The computer 113 also includes an audio frequency generating arrangement 153 which drives the speaker 115. In the preferred embodiment, the frequency generating arrangement 153 includes a conventional software utility routine which is supplied with a frequency value by an application program and which toggles a dedicated digital output line of the computer at the specified frequency, the output line being coupled through a not-illustrated AC coupling capacitor and a variable resistor serving as a volume control to the speaker 115. However, it will be recognized that the arrangement 153 could be implemented as a circuit which accepts a frequency value and generates a sine wave at the specified frequency. The frequency generating arrangement 153 is not in and or itself the focus of the present invention, and thus it is not illustrated and described in detail, because there are known arrangements which can be used to implement it.

FIG. 8 is a graph of a curve 156 showing how the signal strength of the magnetic field generated by the emitter coil 36 varies in a transverse direction with respect to the axis of the coil 36 at a location which is spaced axially from the coil 36 and which represents the typical axial position with respect to the coil 36 of one of the disks 46 and 47 (FIG. 2). The signal strength has a maximum point 157 on the axis of the coil 36, and decreases in strength with progressive movement away from the axis. The maximum gradient or rate of change occurs at points 158 and 159. Conventional systems of the type to which the invention is directed attempt to locate the point 157 of maximum field strength. However, it will be noted that a significant amount of movement along the curve in either direction away from the point 157 is required in order to achieve a detectable change in signal strength. Consequently, it is difficult for a conventional system to achieve accurate alignment with the axis of the coil 36, because reasonably large deviations from proper alignment produce only minor changes in signal strength which are hard to detect.

In contrast, the detecting coils in the inventive guide device 16 of FIG. 2 are all offset radially from the axis of the guide tube 41 which is to be aligned with the coil 36, so that as shown in FIG. 8 they are disposed approximately at the points 158 and 159 when the tube 41 is in a properly coaxially aligned relationship with the axis of the coil 36. In FIG. 2, the lines of flux of the magnetic field diverge as they extend upwardly from the coil 36, and thus the disk 46 is larger than disk 47 and the coils on disk 46 are spaced farther from the tube 41 than the coils on disk 47, so that a line of flux representing the maximum gradient in the magnetic field will pass through a coil on the disk 47 and a coil on the disk 46 when the guide device 16 is properly aligned with respect to coil 36. So long as each detecting coil is disposed at a portion of the curve 156 having a reasonably steep slope, satisfactory operation will be achieved, and the disks could thus be the same size with all of the detecting coils spaced the same distance from the guide tube. However, optimum operation is achieved by locating the coils so that each is disposed at a point of maximum slope or gradient, as at 158 and 159.

It will be recognized that, if the tube 41 is deviated slightly from proper alignment with the axis of coil 36, a significant change in signal strength will occur in certain detecting coils because of the large gradient in the direction of movement of the magnetic field in the region of each such coil, as a result of which the inventive positioning apparatus has a very high sensitivity to positional changes and thus permits the guide device 16 to be coaxially aligned with the coil 36 with a degree of precision previously unknown. Since the disks 46 and 47 are spaced axially, they facilitate precise alignment at two axially spaced points along the tube 41, thus ensuring that the entire tube 41 (as opposed to just the end nearest coil 36) is precisely coaxially aligned with the coil 36.

When using the guide device 16, a user manually holds the guide device 16 so that the tube 41 is approximately in the region of the axis of coil 36, and then watches the LED displays 81 and 82. The upper LED display 81 provides information regarding the accuracy of the positioning of the upper disk 46, and the lower LED display 82 provides information regarding the accuracy of the positioning of the lower disk 47. If the upper disk 46 is precisely coaxial with the axis of coil 36, then the square center LED 91 will be actuated and all of the surrounding arrow-shaped LEDs 86–89 will be off. On the other hand, if the upper disks 46 is not coaxial with the coil 36, the system will turn off the square center LED 91, and will light one of the LEDs 86–89 (or two of them which are adjacent) to indicate the direction in which disk 46 must be moved in order to bring it into coaxial alignment with the axis of coil 36. By moving the entire guide device 16 in the manner indicated by each illuminated arrow-shaped LED, the disk 46 can be brought into coaxial alignment with the coil 36. In a similar manner, the lower LED display 82 provides positional information regarding the lower disk 47.

It will be recognized that illuminated arrow-shaped LEDs on the upper disk 81 and lower disk 82 may simultaneously point in different or opposite directions. So long as each disk is moved in the direction indicated by its own arrow-shaped LED, the guide device 16 will be moved into a position of proper axial alignment. It will also be recognized that, by using the two disks 46 and 47 which respectively effect radial alignment at two axially spaced locations, accurate axial alignment of the guide tube is achieved along its entire length. That is, as opposed to alignment only at a single point, each disk in the inventive device defines a point of alignment, and the two spaced points of alignment together define a line, which permits accurate directional alignment of the line with the axis of the magnetic field and thus the hole through the femoral nail.

The manner in which this is implemented by the computer 113 will now be described with reference to FIGS. 9 and 10, which are flowcharts of the programs stored in PROM 152 of the computer 113. After the system is turned on, program execution is started at 166 in FIG. 9, and at 167 the computer sets up the A/D converter 151. The procedure for setting up an A/D converter is conventional and not essential to an understanding of the present invention, and is therefore not described in detail here. Then, at block 168, the program initializes each of the eight elements C(1) through C(8) of a variable array in RAM 154 to a value of 12,000. As to all such arrays discussed herein, elements 1–4 each correspond to respective detecting coils on the lower disk, and elements 5–8 to respective detecting coils on the upper disk. Then, at 169, the central LEDs 91 and 99 of each LED display are turned off. Also, the keypad interrupt is enabled, which means that the computer will be interrupted when either the ZERO button 106 or the CALIBRATE button 107 is manually pressed. The interrupt routine executed in response to actuation of either of the buttons 106 and 107 is shown in FIG. 10, and will be described before the rest of the main program in FIG. 9 is described, because an understanding of the interrupt routine of FIG. 10 will facilitate a better understanding of the main program of FIG. 9.

The ZERO and CALIBRATE buttons 106 and 107 are used to zero and calibrate the system after it has been turned on and before it is used in association with a patient. Zeroing and calibration are carried out before the nail assembly 11 is implanted in a patient. The operator first holds the guide device 16 as far as possible from the emitter coils in the nail assembly 11, and presses the ZERO button 106. The system then reads and saves the states of the signals from each of the detecting coils as described in more detail below, which represents the unstimulated state of the detecting coils when they are substantially unaffected by the magnetic field being generated by an emitter coil. Then, in a manner described in more detail later, the guide device 16 is oriented in axial alignment with the emitter coil so that the end 44 of the tube 41 is spaced approximately one-half to three-quarters of an inch from the coil, and then the CALIBRATE button 107 is pressed. This causes the system to read and store the state of the signal actually being received from each detecting coil, and as described in more detail hereinafter, the deviations of the guide device 16 from this calibration position are thereafter measured in terms of the difference between signal strength measured by each coil and the stored calibration value of the signal strength for that coil.

Turning now in more detail to FIG. 10, when either the ZERO or CALIBRATE button 106 or 107 is pressed, the program stops whatever it is doing in the main program of FIG. 9, executes the interrupt service routine of FIG. 10, and then returns to the point at which it was interrupted in the main program of FIG. 9. In FIG. 10, the execution of the interrupt service routine begins at 171, and at 172 the computer checks to see if the button pressed is the ZERO button 106. If it is not, then it must be the CALIBRATE button and control proceeds to 173, where the computer causes the speaker 115 (FIG. 5) to issue a beep at 1,000 Hz. Then, at block 174, the computer initializes to zero a variable KH used to specify which of the eight channels in the A/D converter 151 (and thus which of the eight detecting coils) is currently being read. Then, at 176, the variable KH is incremented to a value of one in order to select the first analog channel, and the corresponding value in the previously-mentioned calibration variable array C is set to zero.

Then, at block 177, the program performs a read function (AIN) from the A/D converter 151 to obtain a digital value representing the current magnetic field strength sensed by the associated detecting coil and supplied through the analog signal processing circuit 112 (FIG. 5) to the A/D converter 151. This value is added to the value in the associated element of the calibration variable array C, and the result is stored in that element of the array. Block 178 indicates that block 177 is consecutively executed five times. Thus, the selected element of the calibration variable array ends up containing a sum of five consecutive values of signal strength read from a single detector coil. A sum of five readings is used in order to minimize the effect of momentary noise or other factors which may cause a single reading to be slightly inaccurate.

Then, at block 179, control is returned to block 176, and blocks 176–178 are repeated for the next coil. After eight passes through blocks 176–179, each element of the calibration variable array C will contain the sum of five successive readings of the corresponding detector coil, and control then proceeds from block 179 to block 181, where the computer causes speaker 115 to issue a beep at 1,500 Hz. Blocks 173 and 181 together produce beeps which to a human sound very close together and which are at different frequencies. Thus, the operator hears a two-tone beep which tells him that calibration has been performed. Thereafter, at block 182, control returns to the main program of FIG. 9 at the point in which it was interrupted.

If it was determined at block 172 in FIG. 10 that the button pressed was the ZERO button, then control would proceed to a zeroing routine implemented by blocks 183–190. The zeroing routine is effectively identical to the calibration routine just described above, except that each sum of five readings from a given coil is loaded into a respective element of an eight-element zero variable array Z, rather than into the calibration variable array C.

Referring again now to the main program shown in FIG. 9, following the above-described initialization at blocks 166–169, control enters a main program loop which constitutes the rest of FIG. 9. The first portion of this loop is formed by blocks 194–198, which stores for each coil a sum of five successive readings of the measured signal strength in the same general manner as already described above in association with the calibration and zeroing routines of FIG. 10. The only difference is that each sum is stored in a respective element of a summation variable array SUM, rather than in the calibration array C or the zeroing array Z. After this data has been collected, control proceeds to block 201, where the program initializes to one an index variable N used to indicate for which of the eight detecting coils calculations are currently being performed.

Then, in block 202, the value in the element of the zeroing array Z for the selected coil is subtracted from the corresponding value in each of the summation and calibration arrays SUM and C in order to normalize these values, the thus adjusted value from the summation array SUM is divided by the thus adjusted value from the calibration array C, and the result is stored in one of eight elements of a further variable array B. The index value N is then incremented, and block 203 causes block 202 to be successively executed for each of the eight coils. When this has been completed, the array B contains values representative of normalized signal strengths for the respective coils, and control proceeds from block 203 to block 204.

In block 204, the program calculates a value S1, which is the sum of the absolute values of the first four elements of the array B, and calculates a value S2 which is a sum of the absolute values of the last four elements of the array B. The value S1 thus represents a sum of the normalized magnetic field signal strengths calculated for the four coils on the lower disk 47 (FIG. 2), and the value S2 is a similar sum for the coils of the upper disk 46.

Then, at blocks 206 and 207, successive checks are made to see if either of the values S1 and S2 is equal to zero, and if either is zero then it is set to a very small positive value of 0.1 at 208 or 209 in order to ensure that subsequent division of a number by S1 or S2 is not division by zero which would automatically produce a computer error.

Thereafter, at block 211, the value S1 is divided into four in order to obtain a normalization factor LF for the detecting coils on the lower disk, and the value S2 is divided into four in order to obtain a normalization factor for the detecting coils on the upper disk. Also, variables D, E and F are respectively set to three, three and zero. When the number in variable D is expressed as a four-bit binary number, the least significant through most significant bits respectively indicate the manner in which the arrow-shaped LEDs 94–97 are to be respectively controlled, each LED being turned on when the associated bit is a binary "1" and turned off when the associated bit is a binary "0". Similarly, the variable E controls the four arrow-shaped LEDs 86–89 of the upper display 81. The variable F represents a two-bit number, the least significant bit of which controls the center LED 99 of the lower display 82, and the other bit of which controls the center LED 91 of the upper display 81.

Control then proceeds to block 212, where the absolute value of the normalized signal in array B for coil 63 is compared to the absolute value of the normalized signal strength in the array for coil 61. These are diametrically opposite coils on the lower disk 47. As evident from FIG. 8, if the guide device is properly aligned in a transverse direction extending through two diametrically opposite coils, the coils will each be at points of approximately equal signal strength on the curve 156. On the other hand, if the guide device is not properly aligned in this direction, then both coils would be shifted left or right in FIG. 8, as a result of which one would experience a significantly higher signal strength and the other a significantly lower signal strength. If the comparison in block 212 is found to be true, then in block 213 the value in variable D in increased by three. This addition operation is not a mathematical calculation, but instead a convenient way of manipulating the binary bit pattern in variable D in a manner which effectively turns off one arrow-shaped LED and turns on a diametrically opposite arrow-shaped LED. Block 214 represents a similar comparison for the other two diametrically opposite coils on the lower disk, and blocks 217 and 219 represent similar comparisons for the two sets of diametrically opposite coils on the upper disk. If the comparison conditions in blocks 214, 217 and 219 are found to be true, appropriate adjustments are made to variable D or variable E in blocks 216, 218 and 221.

Control then proceeds to block 222, where the program calculates for each pair of diametrically opposite coils the absolute value of the difference between the normalized signal strengths for the coils in array B, and divides this absolute value by the appropriate normalization factor LF or UF, and then stores the result in a respective difference variable DA, DB, DC or DD.

Then, at block 224, the difference variable DA is checked to see if it is less than 0.1. If it is, then the associated coils are measuring signal strengths which are sufficiently close to each other that they will be deemed to be equal, which means the desired alignment exists in this direction, and thus at 225 a logical AND operation is performed between the variable D and the decimal number 10 (which corresponds to a binary bit pattern of "1010"), as a result of which two bits in the variable D are each forcibly set to binary "0" in order to specify that the associated diametrically-opposed arrow-shaped LEDs should be off, thus indicating that no movement in the directions corresponding to those arrows is needed to bring the guide device into alignment. Similarly, at blocks 226–228, the other difference variables DB, DC and DD are checked and, if less than 0.1, appropriate logical AND operations are carried out in one or more of the blocks 231–233. In blocks 231 and 233, the decimal number 5 corresponds to a binary bit pattern of "0101", and thus forces two bits in the associated variable to 0.

Then, at block 236, the program checks to see if variable D is equal to 0, or in other words whether all four binary bits of this variable are equal to 0. If so, this means that all four of the LEDs on the lower display 82 will be turned off, which in turn means that the center LED 99 should be turned on. Accordingly, at block 237, a logical OR is carried out between the variable F and the decimal value 1 (which corresponds to a binary bit pattern of "01"). This forcibly sets the least significant bit in the two-bit binary value represented by variable F, in order to indicate that the center LED of 99 of the lower display should be turned on. Blocks 238 and 239 do the same thing for the upper display 81, the decimal value of 2 in block 239 corresponding to a binary bit pattern of "10" and thus causing the most significant bit of the 2-bit binary number in variable F to be forcibly set.

Control then proceeds to block 241, where the values in variables D, E and F are loaded into output ports of the computer so that they actually control the various LEDs on the displays 81 and 82 in the desired manner.

Then, still at block 241, the system calculates a sound frequency SF by dividing 300 by the sum of the difference variables DA through DD, selects (as indicated by the function symbol INT) the largest integer which does not exceed the results of the division, and places this integer in the variable SF. The variable SF represents an audio frequency to be output through the speaker 115 to indicate audibly to the operator the extent to which the guide device 16 is out of alignment. It will be noted that as the guide device is moved into alignment, the difference values DA through DD will all decrease toward 0, causing the result of the division in block 241 to yield progressively higher numbers. Thus, sounds at high-pitched frequencies indicate alignment, whereas sounds at lowpitched frequencies indicate substantial misalignment.

A check is made at block 242 to see if the sound frequency SF is above 5,000 Hz, and if so it is limited to 5,000 at block 243 in order to keep the frequency clearly within the normal hearing range of the average person. Then, at block 246, a check is made to see if the normalized value in array B for one of the coils is less than 0.3. If it is, then the guide device 16 is at a location remote from the active emitter coil, and the sound frequency SF is forced at block 247 to a predetermined frequency of 100Hz. At block 248, a check is made to see if the sound frequency SF is less than 100 Hz, and if so it is forced to a value of 100 at block 249 in order to ensure that the sound frequency does not drop below the minimum audible hearing range of the average person.

Thereafter, at block 251, the speaker 115 (FIG. 5) is used to generate an audible sound at the frequency specified by sound frequency variable SF. While the program is in the main loop, the speaker continuously generates an audible sound, the frequency of the sound being updated each time block 251 is executed. The main loop executes in a fraction of a second, and thus the operator is provided audibly and visually with rapid feedback regarding the degree of alignment or misalignment. Control then returns to the start of the main loop at block 194, and the main loop repeats.

It will be recognized that the LEDs in the preferred embodiment described above could be provided directly on the upper sides of the detecting coil disks 46 and 47, although those on the lower disk 47 might be more difficult to see than in the preferred embodiment.

Although the LEDs in the preferred embodiment described above are controlled by the computer 113, it is not absolutely necessary to provide a computer to control them. FIG. 11 is a diagrammatic view of a portion of a system which does not utilize a computer. Portions of FIG. 11 which are identical to portions of the embodiment described above are designated with the same reference numerals, including the lower disk 47, the analog signal processing circuit 112, and the LED display 82. The portion of FIG. 11 which is different involves the provision of an LED control circuit 255 between the analog signal processing circuit 112 and the LED display 82, the circuit 255 essentially replacing the computer 113 of the above-described embodiment. Two outputs of the signal processing circuit 112 respectively corresponding to the diametrically opposite coils 61 and 63 are connected to respective inputs of a differential amplifier 256, the output of which is connected to the negative input of a further differential amplifier 257 and to the positive input of yet another differential amplifier 258, the differential amplifiers 257 and 258 serving as comparators. The positive input of comparator 257 is connected to a voltage divider defined by two resistors connected in series between ground and a source of power, in order to define at the positive input a predetermined threshold voltage. In a similar manner, a threshold is established at the negative input to comparator 258. The source of power at each voltage divider is positive or negative, as appropriate. The output of comparator 257 is connected to the input of a digital inverter 259, and the output of comparator 258 is connected to the input of a digital inverter 261, the outputs of the inverters 259 and 261 being connected to the diametrically opposed LEDs 94 and 96. The inverters 259 and 261 preferably have Schmitt-trigger input circuitry in order to provide some hysteresis in the switching characteristic. If the coils 61 and 63 are sensing approximately equal fields, the amplifier 256 will produce an output of approximately zero volts, which will not exceed the threshold at either of the comparators 257 and 258, and thus they will produce output signals which are viewed as logic high signals by the gates 259 and 261, and both of these gates will produce logic low outputs which turn off the associated LEDs 94 and 96. On the other hand, if the coils 61 and 63 are measuring different field strengths, the output of amplifier 256 will be a positive or negative voltage in dependance on which of the coils is sensing the larger field, and if the voltage is sufficiently positive or negative it will cause one of the comparators 257 and 258 to produce an output voltage sufficiently low to be treated as a logic low signal by the associated inverter 259 or 261, so that the inverter produces a logic high signal which causes the associated LED 94 or 96 to be illuminated in order to indicate the direction in which the disk 47 should be moved in order to equalize the field strengths measured by the two coils 61 and 63. The outputs of the signal processing circuit 112 corresponding to the coils 62 and 64 are connected to a similar arrangement of components at 262–264, 266 and 267, in order to control the LEDs 95 and 97. A NOR gate 268 has four inputs which are each connected to the output of a respective one of the inverters 259, 261, 266 and 267, and as an output which is connected the center LED 99. If all four of the inverters are producing logic low output signals, the NOR gate will output a logic high signal which causes the center LED 99 to be illuminated. On the other hand, if any one of these inverters is producing a logic high signal in order to turn on one of the arrow-shaped LEDs 94–97, the NOR gate 268 will be producing a logic low output signal which will turn off the center LED 99.

FIGS. 12 and 13 show a nail assembly 276 which is an alternative embodiment of the nail assembly 11 of FIG. 2. The bone 12 and femoral nail 21 are the same as in FIG. 2, and are therefore identified with the same reference numerals. A single emitter coil is split into two axially spaced portions 278 and 279, which are fixedly supported in coaxial alignment with each other on diametrically opposite sides of a tubular plastic sleeve 277. The sleeve 277 has diametrically opposite openings 284 and 285. The plastic sleeve 277 is releasably held against rotational or axial movement with respect to the nail 21 so that the coil defined by portions 278 and 279 and the openings 284 and 285 are all coaxially aligned with the openings 26A and 26B in the nail 21. The coil portions 278 and 279 in the illustrated embodiment are windings made from a single elongate piece of thin copper wire with an insulating coating, a portion 281 of the wire extending between the coils to electrically connect them, and portions 282 and 283 of the wire each extending away from a respective portion of the coil to serve as leads. An elongate cylindrical guide rod 286 can be slidably received within the sleeve 277, but is withdrawn before any hole is drilled through the bone 12.

Referring to FIG. 14, an alignment part 291 is provided in order to properly axially align the guide device 16 with the openings 26A and 26B through the nail assembly 277 when the CALIBRATE button 107 is to be pushed in order to calibrate the system. The alignment part has an elongate cylindrical rod 292, and has fixedly secured to one end of the rod a disk-like head 293. The diameter of the rod 292 is slightly smaller than the inside diameter of the opening through the guide tube 41.

An alternative embodiment of the alignment part 291 is shown at 301 in FIG. 15. The alignment part 301 includes a cylindrical rod 302 and a cylindrical rod 303 which are coaxial and have a step 304 between them. The diameter of the rod 302 is only slightly smaller than the inside diameter of the openings 26A and 26B and the nail 12, and the rod 303 has a diameter slightly smaller than the central opening through the guide tube 41.

FIGS. 16–18 show an emitter unit 311 which implements an alternative embodiment of the emitter coil shown at 36 in the embodiment of FIG. 2. The emitter unit 311 has a rectangular flexible sheet 313 made of a nonconductive material, which in the preferred embodiment is a polyimide film. The sheet 313 has eight circular holes 316–323 through it, the holes 316–323 being arranged in a line extending substantially the length of the sheet approximately intermediate the side edges. The holes have diameters which increase progressively in size from hole 316 to hole 323, although each successive increase is relatively small. Also, the spacing between adjacent holes increases progressively from the hole 316 to the hole 323, for a reason which will be explained later.

The sheet 313 has thereon a pattern of thin and flexible copper strips or runs of relatively narrow width. These include a circular coil portion 326 of one turn provided around the hole 316 on the front of the sheet 313, spiral coil portions 327 and 328 of five turns each provided around the holes 320 and 321 on the front side of the sheet, and spiral coil portions 329 and 330 of five turns each provided around the holes 320 and 321 on the rear side of the sheet. Adjacent the hole 320 is a small plated-through hole 334 which electrically connects the radially inner end of the spiral coil portion 327 with the radially inner end of the spiral coil portion 329. A similar small plated-through hole 335 is provided adjacent the hole 321, and electrically connects the radially inner end of the spiral coil portion 328 to the radially inner end of the spiral coil portion 330.

The copper runs also include strips which electrically connect the coils in series, such as strip 336 which is provided on the rear side of the sheet 313 and connects the radially outer ends of spiral coil portions 329 and 330. On the front side of the sheet, as shown in FIG. 16, the copper runs include a strip 337 which connects the radially outer end of spiral coil portion 327 to one end of the circular coil portion 326, a strip 338 which connects the opposite end of the circular coil portion 326 to a plated-through connection hole 341 provided through the sheet 313 adjacent a side edge thereof, and a run 339 which connects the radially outer end of coil portion 328 to a further plated-through connection hole 342 provided adjacent the hole 334. The run 337 has a portion routed to extend parallel to and closely adjacent a portion of the run 338, so that electromagnetic fields generated by these adjacent portions of the runs will effectively cancel each other. For similar reasons, the portions of runs 338 and 339 extending to the holes 341 and 342 are parallel and closely adjacent, and run 336 and a portion of run 339 (disposed on opposite sides of the sheet) are parallel and closely adjacent.

The sheet 313, which is shown in an unrolled configuration in FIGS. 16 and 17, is rolled up during system assembly. For example, the sheet 313 can be rolled from left to right in FIG. 17 so that hole 316 overlays and is aligned with hole 318, hole 318 overlays and is aligned with hole 320, and so forth, resulting in the arrangement shown in section in FIG. 18. It will be noted that the nonuniform spacing between the adjacent holes 316–323 ensures that, in the rolled configuration of FIG. 18, the holes 316–323 are all coaxially aligned with each other along a common axis and collectively define a transverse cylindrical hole through the emitter roll. The slightly different diameters of the holes 316–323 ensure that the transverse cylindrical hole has a substantially uniform diameter despite the fact that different radial layers of the roll have different amounts of curvature. For clarity, the thickness of the coil portions 326–330 are exaggerated in FIG. 18, but it will be recognized that in practice they are very thin in relation to the sheet 313. The coil portions 326–330 which encircle the holes are all necessarily coaxial to the same axis as the holes, and together effectively define a single coil which is functionally equivalent to the coil shown at 36 in the embodiment of FIG. 2. The reason that coil portion 326 has only a single turn, whereas coil portions 327–330 each have five turns, is to provide a total of 21 turns, which in turn yields the appropriate amount of inductance for the overall coil formed by all of the coil portions. As to the portions of the sheet containing holes 317–319 and 322–323, which have no coil portions therearound, in the rolled configuration of the sheet they serve as insulation to prevent two coil portions from engaging a metal part or each other in a manner creating a short.

The holes or terminals 341 and 342 are connected by wires to the control unit 18 (FIG. 1). After the wires have been connected to the holes 341 and 342 and the sheet 313 has been rolled up, it can be inserted directly into the plastic sleeve 31 (FIG. 2) so that the holes 316–323 are in alignment with the holes 32 in the sleeve 31, the sleeve 31 preventing any significant unrolling of the sheet 313. Alternatively, prior to inserting the rolled sheet 313 into the sleeve 31, a strip of polyamide film with an adhesive layer on it could be wrapped circumferentially around the rolled sheet 313 in order to positively prevent it from unrolling, after which the rolled sheet with the film around it can be inserted into the sleeve 31.

When an electrical potential is applied between the holes 341 and 342, an electric current flows from hole 342 through run 339 and coil portion 328, through plated-through hole 335 to coil portion 330 on the opposite side of the sheet, through run 336, coil portion 329 and hole 334 to the coil portion 327, and then through run 337, coil portion 326 and run 338 to the hole 341. As a result, the overall coil formed by the coil portions 326–330 produces an electromagnetic field which is used to align the drill so that, as the drill bores through the bone, it passes coaxially through all of the aligned holes 316-323 in the rolled sheet 313.

Those of ordinary skill in this art will recognize how to make the emitter unit 311. Rogers Corporation of Chandler, Arizona sells under the name R/flex$^3$ 2000 a flexible circuit laminate having a center which is the polyimide sheet 313 and having adhesively secured to opposite sides of this sheet respective thin copper layers. Dupont sells a similar product under the name KAPTON. The necessary holes 316–323, 334–335 and 341–342 are each punched or drilled in this conventional and commercially available component, the holes 334–335 and 341–342 are then plated through with copper in a conventional manner, art work is thereafter applied to the copper sheets on opposite sides of the laminate, and then the resulting pattern is etched in a conventional manner in order to leave the coil portions 326–330 and the runs 336–339. It will be recognized that there may also be other ways to fabricate the emitter unit 311.

The emitter unit 311 of FIGS. 16–18 has the advantage of providing repeatability and reliability in yielding a given coil configuration, because the coil is an image etched from a negative rather than a wire wrapped by hand. Further, the emitter unit efficiently utilizes space, because the etching approach is superior to handwrapping in reducing air gaps, and coil portions are etched on both sides of the substrate. The reliability with which a given coil configuration can be repeated may simplify or even eliminate the need to calibrate the control circuit, because coil variances are minimized. It should also be noted that, when the emitter unit 311 is in the coiled configuration of FIG. 18, it has not only a transverse radial hole which is defined by holes 316–323 and through which a drill can pass, but also has perpendicular thereto a central axial hole 344 through which a guide wire or guide rod can pass.

FIGS. 19 and 20 depict an emitter unit 351 which is an alternative embodiment of the emitter unit 311 shown in FIGS. 16–18, and which is shown in an unrolled configuration. The emitter unit 351 is similar to the emitter unit 311, and therefore only the differences will be mentioned. The emitter unit 351 has a sheet 353 which is shorter in length than the sheet 313 of the emitter unit 311, and which has only two holes 356 and 357 therethrough. Respective spiral coil portions 361–364 are provided around the holes 356 and 357, each coil portion having five and one half turns so that the resulting effective coil has a total of twenty-two turns. Two small plated-through holes 366 and 367 each adjacent a respective one of the holes 356 and 357 electrically connect the radially inner ends of the spiral coil portions provided around each of holes 356 and 357 on opposite sides of the sheet. A run 371 connects the radially outer ends of the coil portions 363 and 364, and two runs 372 and 373 connect the radially outer ends of the coil portions 362 and 361 to respective plated-through terminal holes 377 and 376. When the emitter unit 351 is rolled up, it is rolled so that the edges 378 and 379 at opposite ends of the sheet 353 are disposed adjacent each other, and thus the sheet 353 essentially forms a cylindrical tube. Both sides of the sheet, including the coil portions 361–364 and connections 371–373, are preferably covered with a polyimide film, which serves as an insulator to prevent the coil portions 361–364 from contacting other structure that could produce an electrical short.

FIG. 21 is a block diagram of an alternative embodiment of the control unit 18 shown in FIGS. 1 and 5. Similar elements have been designated with similar reference numerals, and only the differences will be described here.

More specifically, a clock signal CLK on line 391 and three programmable gain control signals PGA on line 392 are supplied from the computer 113 to the analog signal processing circuit 112. The PGA control lines 392 permit the computer 113 to control the gain of the analog outputs supplied by the analog signal processing circuit 112 to the A/D converter 151 in the computer 113, and the clock signal CLK on line 391 is used by the computer 113 to notify the analog signal processing circuit 112 that the programmable gain specified by line 392 is being changed, as described in more detail later. The computer 113 also includes, in addition to the ZERO and CALIBRATE buttons 106 and 107, a SENSITIVITY thumbwheel 393 which is used to specify a sensitivity level, as described in more detail later.

Figure 22:
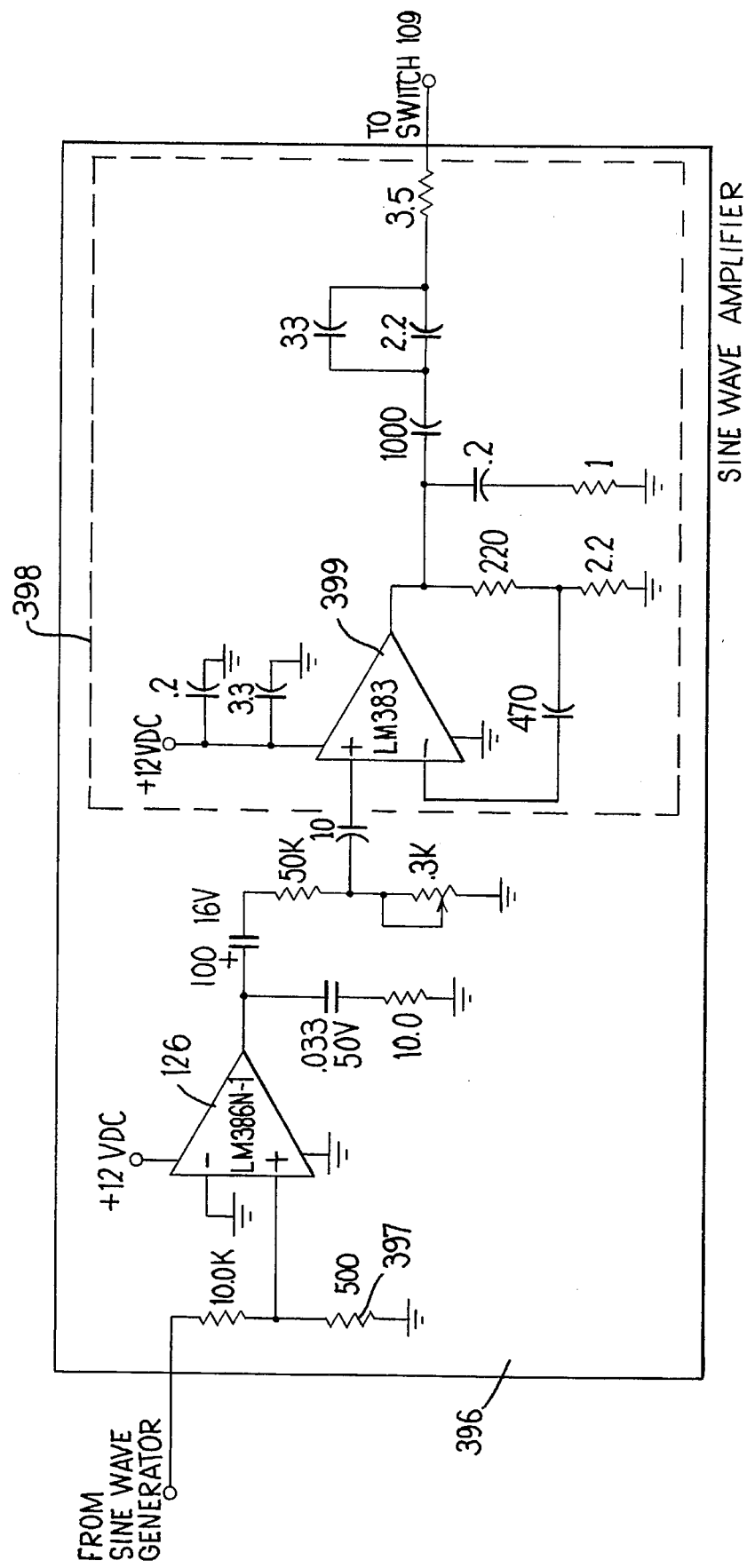

The sine wave amplifier shown at 123 in FIG. 5 and having a sensitivity switch 108 has been replaced with a sine wave amplifier 396 which does not have a sensitivity switch and which is shown in more detail in FIG. 22. The sine wave amplifier 396 includes most of the circuitry of the sine wave amplifier 123, except that the switch 108 and associated resistors 127 and 128 have been replaced with a single 500 Ω resistor shown at 397 in FIG. 22. The sine wave amplifier 396 also includes some additional circuitry, which is shown at 398 and includes an operational amplifier 399.

The analog signal processing circuit 112 of FIG. 21 is shown in more detail in FIG. 23. Except as described below, this circuit is similar to the circuit shown in FIG. 7. The filter and amplification circuit shown at 401 in FIG. 23 includes substantially all of the components of the corresponding circuit shown at 132 in FIG. 7, but also includes a programmable gain amplifier 402 provided between the operational amplifiers 138 and 139, along with associated support circuitry. In the preferred embodiment, this integrated circuit is a PGA100BG available from Burr-Brown of Tucson, Ariz. The amplifier 402 has an analog input INO which is coupled to the output of the operational amplifier 138, an analog output VO which is coupled to the positive input of the operational amplifier 139, amplification control inputs A3–A5 to which are applied the PGA control lines 392 received from the computer 113 through the connector 146, and a clock input CP to which is applied the clock signal CLK received from the computer 113 on line 391. The gain control and clock inputs are all digital inputs. The leading edge of a signal on the CLK line 391 clocks into the PGA 402 the gain control information present on the PGA control lines 392.

The resistor 403 connecting the output of the modulation circuit 133 to the input of the final amplification circuit 406 has a value of 11K. The resistor 403 has a value of 11K for the signals from only four of the detectors coils, and has a value of 52K for the signals from the other four detector coils, as shown for example at 404.

The final amplification circuit 406 is similar to the final amplification circuit 134 in FIG. 7, except that a resistor at 407 has been changed to have a value of 100K.

FIGS. 24–27 are flowcharts representing a modified version of the program depicted in FIGS. 9 and 10. The modifications implement automatic gain control so that the computer 113 can adjust the signals received from the detector coils to provide a signal which is suitably strong but which does not saturate the input circuits of the analog to digital converter.

Figure 24:
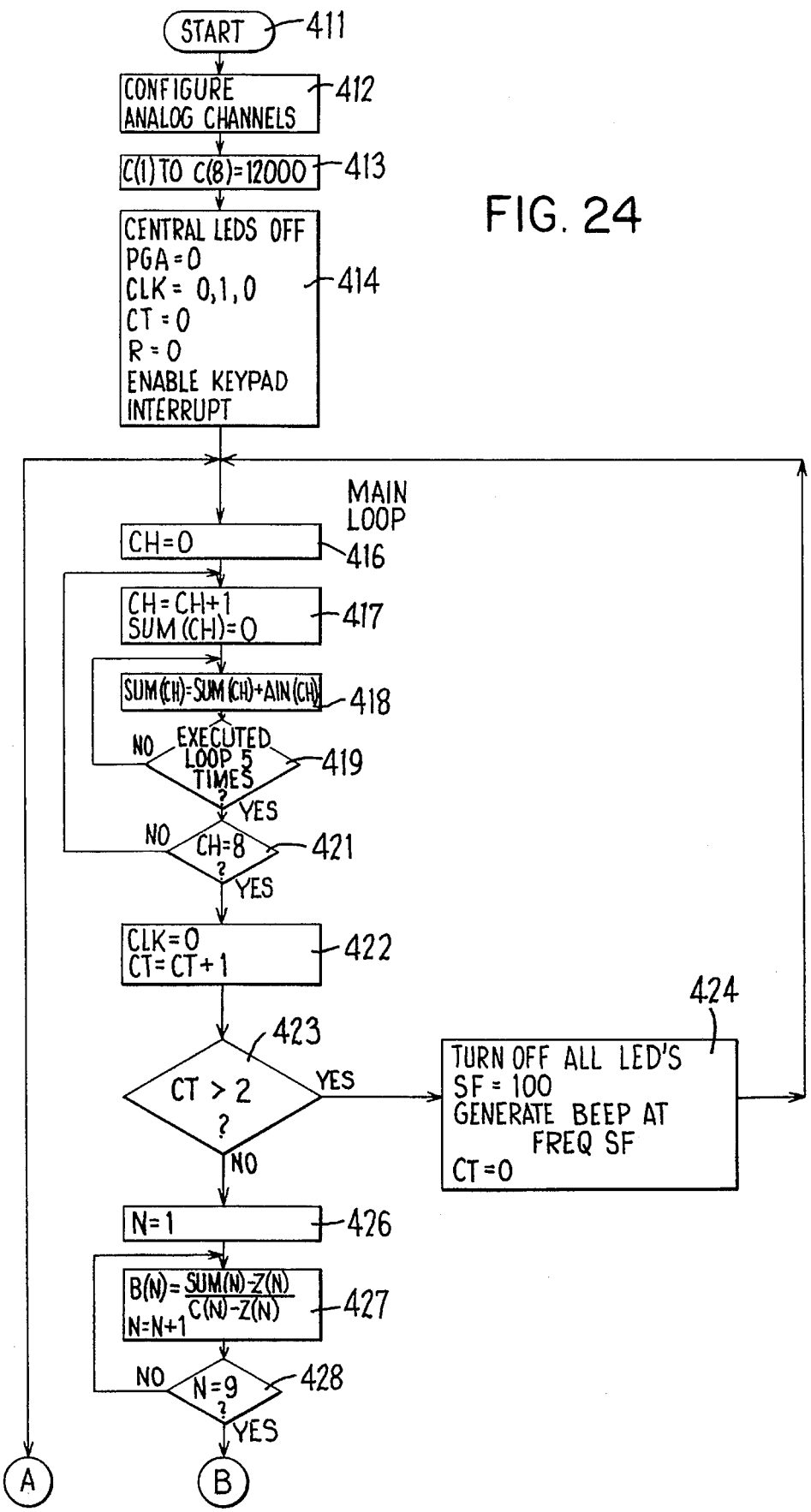

After the system is turned on, program execution is started at 411 in FIG. 24. Then, blocks 412 and 414 are executed, which correspond to blocks 167 and 168 in FIG. 9 and are therefore not described in detail. Then, in block 414, the central LEDs 91 and 99 (FIG. 5) of each LED display are turned off. Then, the computer outputs on the PGA lines 392 a value of zero, which represents a normal gain level and will be viewed herein as being a relative gain of 1. Then, the computer causes the signal on the CLK line 391 to transition from a logic low to a logic high and then back to a logic low, which in turn causes each of the PGA amplifiers 402 to accept and implement the gain specified by the PGA lines 392. Still in block 414, a count value CT is initialized to zero, and a variable R is set to zero. Then, the keypad interrupt is enabled so that the computer will be interrupted when either the ZERO button 106 or the CALIBRATE button 107 is manually pressed. Then, the program begins a main program loop by proceeding to block 416.

Control proceeds through blocks 416–419 and 421, which are similar to blocks 194–198 in FIG. 9, and in which the computer reads in signals from each of the eight detection coils and stores a signal strength for each coil in a respective element of the summation variable array SUM.

Then, at block 422, the CLK line output 391 of the computer is forced to a logic low. In the present discussion, the main loop of the program was entered from block 414, where the value of the CLK line had already been set to a logic low, but in some cases control returns to the start of the main loop at block 416 with the value of the CLK line 391 at a logic high, and thus at block 422 the CLK line will be forced to a logic low. Then, also in block 422, the count CT is incremented.

In block 423, the computer checks to see if the count value CT is greater than 2. As will become evident from the discussion which follows, if the count value CT exceeds a value of 2, it means the signals received by the computer from the detector coils are too weak to be meaningful, and should not to be used to control the LEDs. Therefore, if the count value CT is greater than 2, control proceeds to block 424, where the computer turns off all of the LEDs, generates a beep at 100 Hz, and sets the count value CT to zero. Then, control returns to the beginning of the main loop at 416.

On the other hand, if the count value CT is at or below a value of 2, control proceeds to blocks 426–428, which are identical to blocks 201–203 in FIG. 9 and in which the measured signal strengths are normalized, and the normalized values are stored in array B. From block 428, control proceeds to block 431 in FIG. 25. When FIG. 25 is entered, the count variable CT will always contain a value of either 1 or 2.

Figure 25:
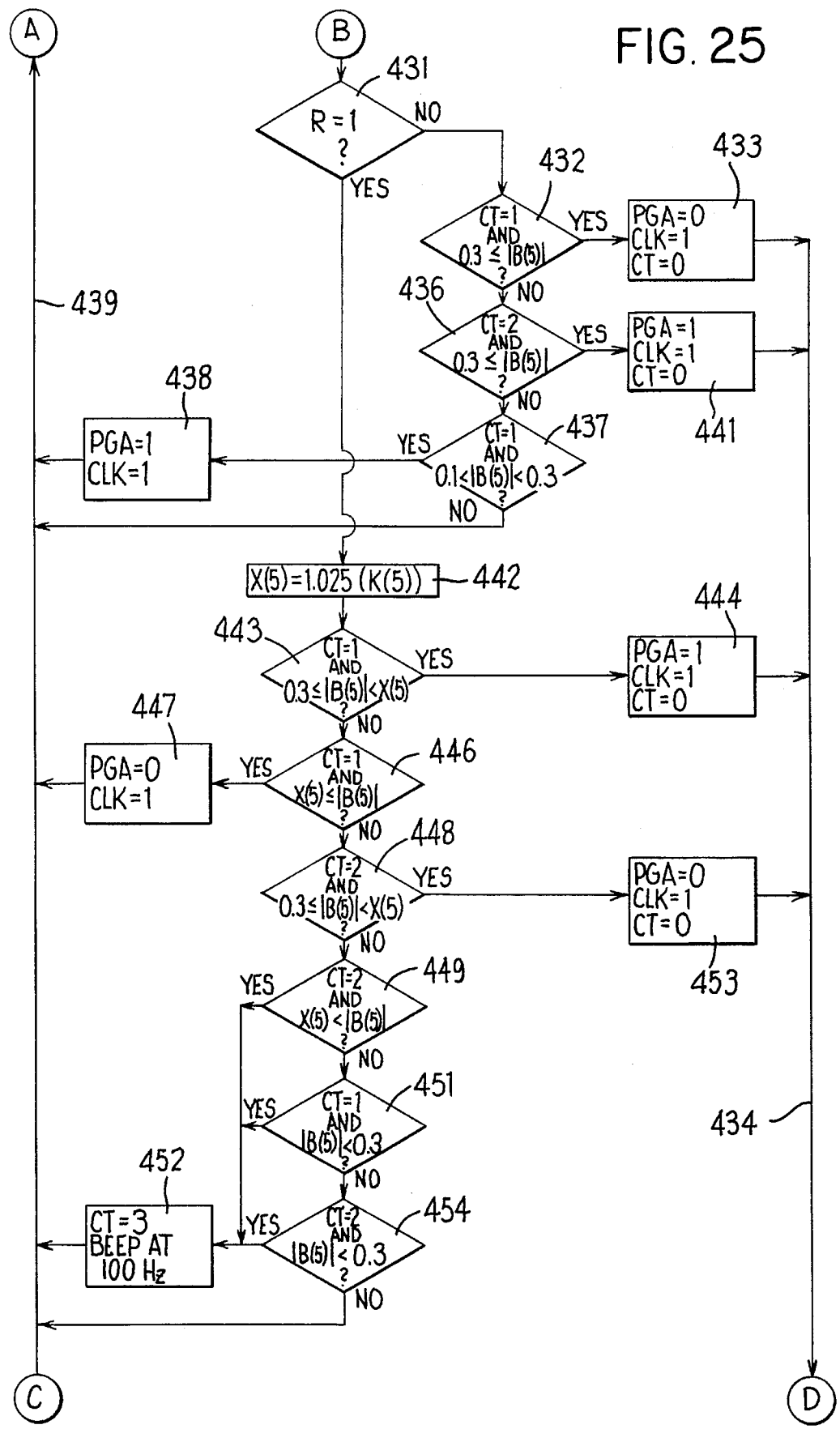

FIG. 25 represents a portion of the program which determines whether or not the signals from the detecting coils are too weak or too strong, and thus not suitable for use in controlling the LEDs. If the signals are too weak or too strong, the computer makes an appropriate adjustment to the gain of the variable gain amplifiers 402 (FIG. 23) and then checks to see if signals of acceptable strength are being received. When signals of suitable strength are being received, control will ultimately proceed to the routine of FIG. 26, which sets the LEDs in an appropriate manner. On the other hand, whenever it is determined in FIG. 25 that the signal strengths are not currently acceptable, control is returned to the beginning of the main loop. For purposes of evaluating signal strength, the signal from one of the coils on the lower disk 47 (FIG. 2) is used, the normalized signal strength for which is located in array element B(5).

Looking more closely at FIG. 25, at block 431 the computer checks to see if the variable R has a value of 1. The variable R normally contains the gain control value PGA which was in effect at the point in time when the indicator LEDs were most recently updated. During normal operation, the variable R will thus usually contain a value which is the same as the gain control value PGA, but if the gain value is changed then the variable R will be different from the gain until such time as the routine controlling the indicator LEDs is again executed, because the variable R is loaded with the gain value PGA at the end of the routine controlling the LEDs.

Assuming that the routine of FIG. 25 is being executed for the first time following initialization, the variable R will have been initialized to 0, and thus control will proceed from block 431 to block 432, where the computer will check to see if the count CT has a value of 1 and the absolute value of the signal strength from the selected coil is above a minimum acceptable signal strength of 0.3. If so, then the magnitude of the signal strength is sufficient to serve as a basis for controlling the LEDs, and control proceeds to block 433, where the system outputs on the gain control lines PGA a value of 0, (corresponding to a relative gain of 1), and sets the CLK line 391 to a logic high to load this gain value into the programmable gain amplifiers 402 (FIG. 23). Then, the count CT is reset to 0, and control proceeds at 434 to the routine of FIG. 26, which controls the LEDs and will be described later.

If the conditions specified in block 432 are not met, control proceeds to block 436, where the conditions will not be met during this pass because the count value CT will be 1 rather than 2, and control proceeds to block 437, where the computer checks to see if the count value CT is 1 and the absolute value of the signal strength B(5) is between values of 0.1 and 0.3. If the signal strength is between these values, then it is currently too low to be used in controlling the LEDs, but could possibly be acceptable if the gain were increased. Therefore, control proceeds to block 438, where the computer outputs on the gain control lines PGA a value of 1 (representing a relative gain of 2), and then sets the CLK line 391 to a logic high to load the new gain setting into the amplifiers 402 (FIG. 23). Control then returns at 439 to the start of the main loop at block 416 in FIG. 24. As execution continues, it will be noted that, in block 422, the CLK output is returned to a logic low and the count value CT is incremented from a value of 1 to a value of 2.

When control again reaches block 431 in FIG. 25, the variable R will still have a value of 0, even though the gain control value PGA is 1, because as mentioned above the variable R is not updated to conform to PGA until the LED control routine is executed. Thus, control will proceed from block 431 to block 432, and because the count variable CT now contains a value of 2, control will proceed from block 432 to block 436. At block 436, the computer checks to see if the count CT is 2 and if the absolute value of the signal strength is now greater than the value 0.3. If so, then the increased gain has brought the signal strength to a value sufficient to permit the LEDs to be updated using the signals from the detector coils, and control proceeds to block 441, where the computer outputs a value of 1 on the gain control lines PGA, sets the CLK signal to a logic high to load the new gain value into the amplifier, and then sets the count value CT to 0. Control then proceeds at 434 to the LED control routine. Once the LED control routine has been executed with the higher gain, the variable R will be loaded with the PGA value of 1, and thus when the routine of FIG. 25 is entered again, control would proceed from block 431 to block 442.

When the higher gain is in effect, it is important to ensure that the received signal is not above a value which will saturate any circuitry. Therefore, at block 442, a value K(5), which is described later and represents the maximum expected signal strength from the detector coil monitored by the routine of FIG. 25, is multiplied by a value of 1.025 in order to obtain an upper limit value slightly in excess of the maximum expected value, and the upper limit value is stored in a variable X(5). Control then proceeds to block 443, where the computer checks to see if the count value CT is 1 (meaning that the gain has not just been changed) and whether the absolute value of the measured signal strength B(5) is between 0.3 and the upper limit in variable X(5). If it is, then control proceeds to block 444, where the system controls the PGA lines and the CLK line so as to ensure that the higher gain setting is in fact in effect, and then clears the count value CT. Control then proceeds at 434 to the LED control routine.

If the conditions specified in block 443 are not both true, then control proceeds to block 446, where the computer checks to see if the count value CT has a value of 1 and the absolute value of the signal strength B(5) is in excess of the upper limit in variable X(5). If these conditions are met, then the signal is so strong that it could saturate some circuitry and produce erroneous results. Accordingly, control proceeds to block 447, where a value of 0 is output on the PGA lines and the CLK output line is set to a logic high, which causes the amplifier 402 (FIG. 23) to change from a relative gain of 2 back to a relative gain of 1. Control then returns at 439 to the main routine without entry to the LED control routine.

If the conditions at block 446 are not met, control proceeds to blocks 448 and 449, where the conditions will not usually be met because the count variable CT will normally have a value of 1. Thus, control will reach block 451, where the computer will check to see if the count variable CT is 1 and the absolute value of the signal strength B(5) is below the value of 0.3. If these conditions are met, it means that the system is operating at the increased gain level but the received signal strength is still not strong enough to be used to control the indicator LEDs, and thus control proceeds to block 452 where the count variable CT is set to a value of 3 and a beep is generated at 100 Hz to notify the system operator that the signal strength is insufficient. Control is then returned at 439 to the beginning of the main loop at block 416. Subsequently, at block 423, it will be determined that the count variable CT has a value greater than 2, and block 424 will be executed to turn off all of the indicator lights.

In FIG. 25, if the gain is reduced from a relative gain of 2 to a relative gain of 1 at block 447 and control then returns to the main routine, then when control again reaches block 431 at the top of FIG. 25 the variable R will still be 1 but the count variable CT will now have a value of 2, and control will thus proceed through blocks 431, 442, 443 and 446 to block 448, where the computer will determine that the count variable CT has a value of 2 and will check to see if the absolute value of the signal strength B(5) is in a range between 0.3 and the upper limit of X(5). If it is in this range, then the signal strength is now at an acceptable value for purposes of controlling the LEDs, and control proceeds to block 453, where the computer uses the PGA and CLK lines to ensure that the lower gain is in fact in effect, and clears the count variable CT. Control then proceeds at 434 to the routine which controls the indicator LEDs.

If the conditions in block 448 are not met, then control proceeds to block 449, where the computer determines that the count variable has a value of 2 and checks to see if the absolute value of the measured signal strength B(5) is still in excess of the upper limit X(5) despite the gain decrease, in which case the LEDs cannot be accurately updated and control proceeds to block 452.

Alternatively, if the conditions are not met in block 449, control would proceed through block 449 to block 454, where the computer verifies that the count variable CT has a value of 2 and checks to see if the absolute value of the signal strength B(5) is below the minimum acceptable value of 0.3. If these conditions are met, it means that the reduction in gain has taken the signal strength from a value in excess of the upper limit at the higher gain to a value below the minimum acceptable level of 0.3 at the lower gain. Therefore, the LEDs cannot be accurately updated and control proceeds to block 452.

Figure 26:
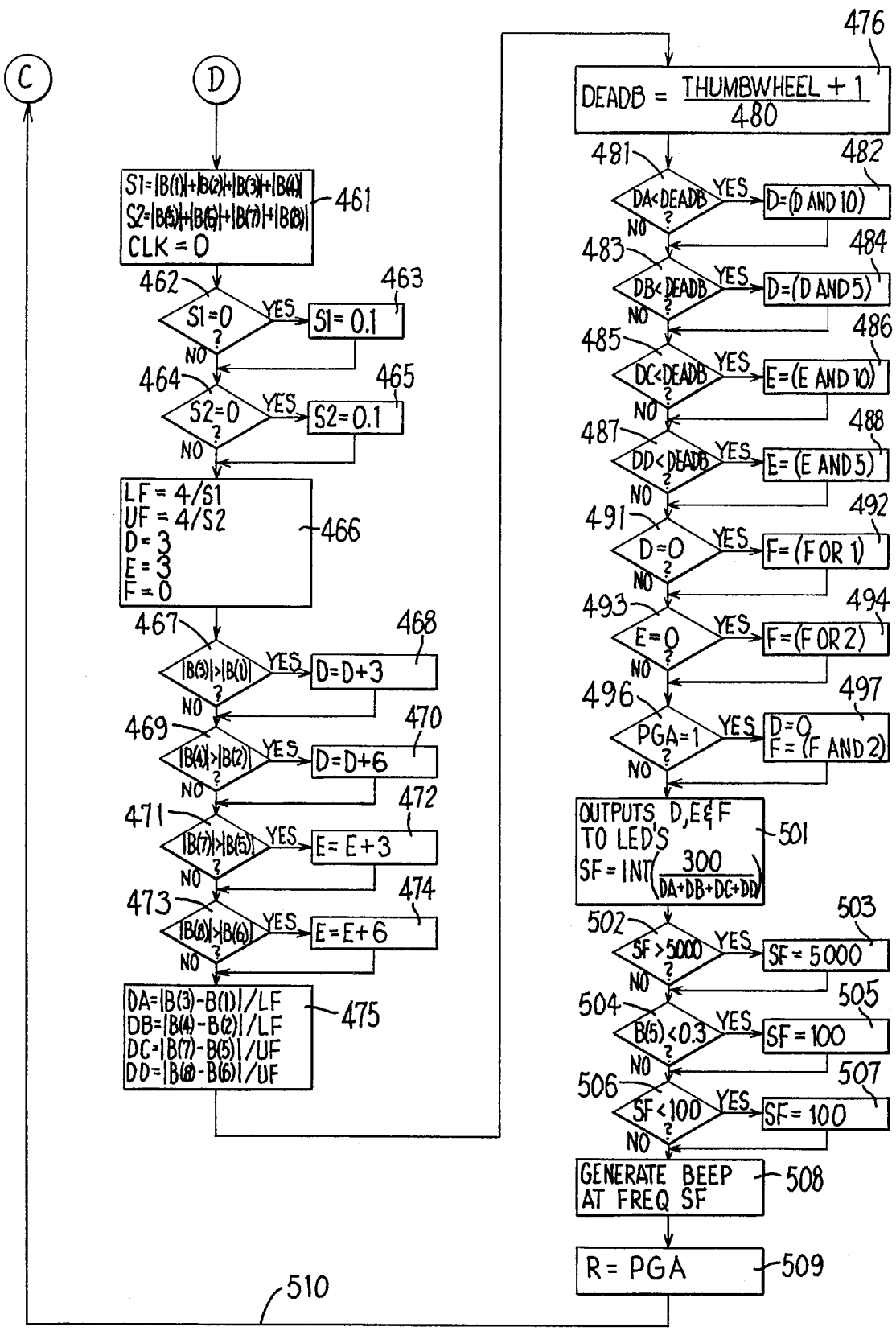

Blocks 433, 441, 444 and 453 all represent circumstances under which control proceeds to the routine of FIG. 26, which controls the indicator LEDs. In FIG. 26, execution begins at block 461, which is identical to block 204 in FIG. 9, except that it also sets the CLK line 291 back to a logic low (to complete the pulse on the CLK line which was initiated when it was set to a logic high in one of the blocks 433, 441, 444 and 453 of FIG. 25). Control then proceeds to block 462. Blocks 462–475 are identical to blocks 206–209, 211–214, 216–219 and 221–222 in FIG. 9, and are therefore not described here in detail.

From block 475, control proceeds to block 476, where the computer reads the setting of the thumbwheel 393 (FIG. 21), adds one to this value, divides the sum by 480, and stores the result in a variable DEADB which represents a deadband value. The deadband value DEADB defines a radial deviation limit. Control then proceeds to block 481. Blocks 481–488 are identical to the blocks 224–228 and 231–233 of FIG. 9, except that the values DA, DB, DC and DE are each being compared to the variable DEADB rather than a fixed value of 0.1. Since the variables DADD represent differences between respective pairs of opposed detecting coils, the comparisons in blocks 481, 483, 485 and 487 represent the extent to which signal magnitudes from two opposed coils can shift away from equal readings before the computer concludes that a center LED should be turned off and one of the arrow-shaped LEDs should be turned on to indicate a needed positional correction of the drill guide. Stated differently, these comparisons determine how far the drill guide can be moved out of axial alignment in a radial direction before an arrow LED is illuminated. It will thus be recognized that, by adjusting the thumbwheel, the value in the variable DEADB can be changed, which in turn adjusts the extent to which the drill guide can be moved away from axial alignment before one of the arrow LEDs is illuminated. Thus, changing the value on the thumbwheel changes the sensitivity of the system.

From blocks 487 and 488, control proceeds to block 491. Blocks 491–494 are effectively identical to blocks 236–239 in FIG. 9, and are not described here in detail.

Control then proceeds to block 496, where the computer checks to see if the current gain control value PGA has a value of 1 (which corresponds to a relative gain of 2). When the system is operating at the higher gain, the drill guide is usually spaced from the emitter coil, and the signals from the detector coils on the lower disk 47 (FIG. 2) are sufficiently strong but the signals from the detector coils on the upper disk 46 are too weak. Therefore, when operating at the increased gain, the signals from the detector coils on the upper disk are ignored, and consequently the LEDs on the upper disk-like display 81 (FIG. 2) are all turned off, and only the LEDs on the lower display 82 are utilized. Thus, if it is determined at block 496 that PGA has a value of 1, control proceeds to block 497 where the computer sets the variable D to zero in order to turn off the arrow-shaped LEDs for the upper display 81, and clears the bit in variable F which controls the center LED for the upper display 81 in order to turn off this center LED. Control then proceeds to block 501. Blocks 501–508 are identical to blocks 241–243, 246–249 and 251 in FIG. 9, and are therefore not described here in detail.

From block 508, control proceeds to block 509, where the variable R is loaded with the current PGA value to reflect the fact that the LED control routine has been executed at least once with the system operating at the gain now specified by variable R. Control then returns at 510 to the beginning of the main routine at block 416 in FIG. 24.

Figure 27:
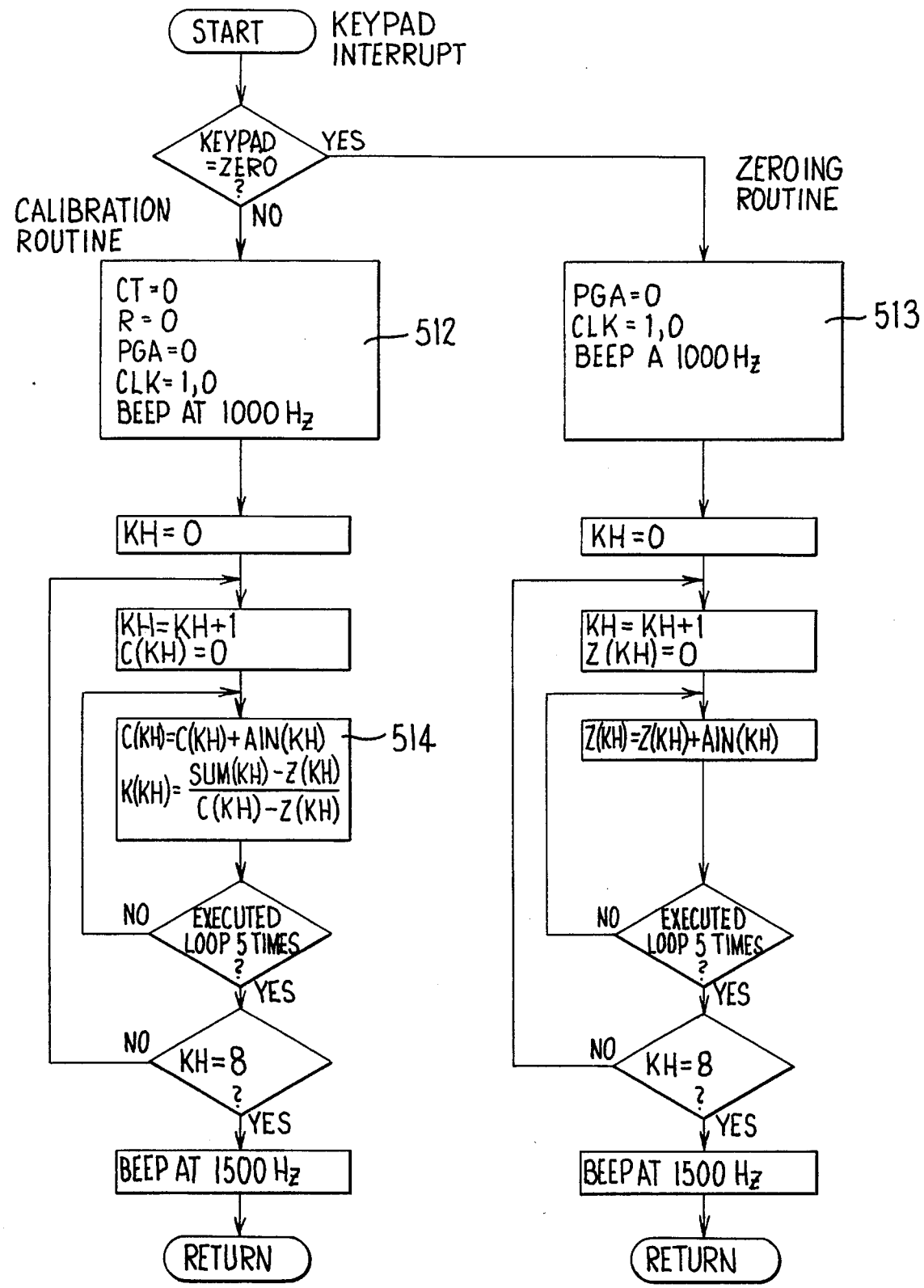

FIG. 27 is a flowchart of the interrupt service routine executed when either the ZERO button 106 or the CALIBRATE button 107 is manually pressed. The interrupt service routine of FIG. 27 is identical to the interrupt service routine of FIG. 10, except for the following differences. Block 512 in FIG. 27 corresponds to block 173 of FIG. 10, in that it includes generation of a beep at 1000 Hz, but in addition it sets the count value CT to 0, sets the variable R to 0, outputs a 0 on the PGA lines 392 in order to force the system to a relative gain of 1 for purposes of calibration, and changes the CLK line 391 to a logic high and then back to a logic low in order to clock the new gain into the gain amplifiers 402 (FIG. 23) and thus forcibly implement a relative gain of 1.

Block 513 in FIG. 27 corresponds to block 183 in FIG. 10, in that it generates a beep at 1000 Hz, but in addition it outputs a 0 on the PGA lines 392 and then successively outputs a logic high and logic low on the CLK line 391 in order to forcibly implement a relative gain of 1.

Block 514 in FIG. 27 corresponds to block 177 in FIG. 10, in that each of the eight elements in the C array is loaded with data which represents a signal strength from the corresponding detector coil. In addition, the value in the element of the zeroing array Z for each coil is subtracted from the corresponding value in each of the summation and calibration arrays SUM and C in order to normalize these values, the thus adjusted value from the summation array SUM is divided by the thus adjusted value from the calibration array C, and the result is stored in one of the eight elements of a variable array K. The data in the array K is thus similar to the data loaded into the array B in block 427 of FIG. 24, in that the values in each case represent normalized signal strengths for the respective coils. However, since the array K is loaded when the drill guide is in a calibration position of the type shown in FIGS. 14 and 15, the detector coils will be as close to the emitter coil as they are normally permitted to get, and thus the values in the array K represent the maximum signal strengths which the detector coils should ever experience from the emitter coil. As described above, the maximum value in array element K(5) is used in block 442 of FIG. 25 to determine the upper limit value placed in variable X(5).

FIGS. 28 and 29 shown an alternative embodiment of the guide device 16 of FIG. 1. In FIGS. 28 and 29, a plastic housing 521 has a teardrop-shaped upper portion 523, and a handle portion 522 extending horizontally outwardly from the pointed end of the teardrop-shaped upper portion. A downwardly converging frustoconical lower portion 524 extends downwardly from the underside of the upper portion 523. A cylindrical sleeve 526 extends vertically through the housing, and is secured to top and bottom walls 527 and 528 of the housing. Disks 531 and 532 each having thereon four detector coils are mounted at vertically spaced locations on the sleeve 526 within the housing.

A vertically extending guide tube 536 has an upper portion 537 with an outside diameter slightly less than the inside diameter of the sleeve 526, and has a lower portion 538 with an outside diameter substantially equal to the outside diameter of sleeve 526. An annular step 539 is located between the portions 537 and 538. The tube 536 has at its lower end a plurality of teeth 541, and has a central opening 542 of uniform diameter extending vertically therethrough. The upper portion 537 is removably slidably inserted into and has approximately the same axial length as the sleeve 526, the annular step 539 being disposed against the lower end of the sleeve 526. Withdrawal of the tube 536 from sleeve 526 is yieldably resisted by friction between them. The tube 536 can be manually withdrawn from sleeve 526, and replaced with other tubes which are identical to tube 536 except that the lower portion 538 of each has a longer or shorter axial length. Thus, in use, an appropriate tube is selected so that the axial length of the lower portion corresponds to the depth of tissue or muscle through which the guide must be inserted to reach the bone, a longer length being used for patients with a thick layer of tissue, and shorter lengths for patients with progressively thinner layers of muscle and tissue.

The LEDs 546–550 corresponding to the upper disk 531 and the LEDs 551–555 corresponding to the lower disk 532 are provided in the top wall 527 of the housing 521 on opposite sides of the sleeve 526. A cable 557 exits from the handle portion 522 and contains wires which are coupled to the LEDs and to the detector coils.

The housing 521 has two different color bands 558 and 559 on the exterior thereof, which respectively represent the upper and lower detector disks 531 and 532 disposed inside the housing. The LEDs 546–550 for the upper disk 531 all have the same color as the upper color band 558, and the LEDs 551–555 for the lower disk 532 all have the same color as the lower color band 559. Thus, when one of the arrow-shaped LEDs 547–550 is illuminated, the operator knows that it is the upper end of the housing which needs to be positionally adjusted because of the corresponding color band 558 on the upper portion of the housing, whereas when one of the arrow-shaped LEDs 552–555 is illuminated, the operator knows that the lower portion of the housing should be positionally adjusted because of the corresponding color band 559 on the lower portion of the housing.

FIG. 30 is a top view of a portion of an alternative embodiment of the housing 521 of FIG. 28, the modified housing including a top wall 571 having a cylindrical vertical sleeve 572 which is equivalent to the sleeve 526 of FIG. 29. An inner ring of LEDs includes four arrow-shaped LEDs 581–584 at equally spaced angular intervals, with small circular LEDs 585 therebetween. An outer ring includes four arrow-shaped LEDs 576–579 with small circular LEDs 580 therebetween. The rings are concentric about the sleeve 572. The LEDs 576–580 correspond to the upper disk in the housing, and the LEDs 581–585 correspond to the lower disk. Since the sleeve 572 is at the center of the LED arrangement, there is no central LED. Instead, all of the small circular LEDs 585 of the inner ring are simultaneously turned on and off at the points in time when the corresponding center LED of the prior embodiments would have been turned on and off, and all of the small circular LEDs 580 of the outer ring are simultaneously turned on and off at points in time when the corresponding center LED of the prior embodiments would have been turned on and off. In the embodiment of FIG. 30, the housing has color bands similar to those shown at 558 and 559 in FIG. 28 and the respective rings of LEDs have respective colors corresponding to the respective color bands, but it will be recognized that it would be possible to use a common color for the LEDs of both rings and omit both color bands.

As discussed above in association with FIGS. 28 and 29, the guide tube 536 is one of several similar tubes. FIG. 31 shows the guide tube 536 and two similar guide tubes 536A and 536B. As mentioned above, guide tubes 536A and 536B are substantially identical to guide tube 536 with respect to the upper portion 537 above the step 539 of guide tube 536, and the tubes differ only in that the portion 538 below the step 539 of guide tube 536 is axially longer than the corresponding portion 538A of guide tube 536A and is axially shorter than the corresponding portion 538B of guide tube 536B.

OPERATION

After turning on the system of FIG. 1, and before installing the femoral nail 21 in the bone of a patient, the drill guide device 16 is first held at a location very remote from the femoral nail 21 and thus remote from the magnetic field being generated around the femoral nail 21, and the ZERO button 106 is pressed. Then, with reference to FIG. 14, the cylindrical rod 292 of the alignment part 291 is inserted through the opening in the guide tube 41 of guide device 16, and then the lower end of rod 292 is inserted through the openings 26A and 26B in the femoral nail 12 so that the nail 12 and the lower end of rod 292 each engage an upwardly facing surface 294. The upper end of the guide device 16 is maintained against the underside of the head 293 either manually or by friction between the guide tube 41 and rod 292, so that the lower end 44 of the guide tube 41 is spaced a predetermined distance from the upper end of nail 12. Alternatively, the alignment part 301 of FIG. 15 could be used, in particular by inserting the rod 302 through the openings 26A and 26B with a very close fit therebetween, orienting the parts so that the nail 12 and lower end of rod 302 engage the surface 294, and then slipping the guide device 16 over the rod 303 so that the lower end 44 of the guide tube 41 engages the step 304. It will be noted in FIG. 15 that the lower end 44 of the guide tube 41 is spaced the same predetermined distance from the nail 12 as in FIG. 14. With the selected alignment part aligning the guide device 16 and nail 12 as shown in either FIG. 14 or 15, the CALIBRATE button 107 is pressed. Thereafter, the nail assembly 11 is driven lengthwise into the patient's femur.

The drill guide 16 (FIG. 2) is then manually held close to the surface of the patient's leg, and its position is varied while the LEDs are visually observed. Depending on the size of the patient's leg, the SENSITIVITY switch 108 can be set to select an appropriate gain reflecting the distance from the skin surface to the bone. Illuminated arrow-shaped LEDs indicate the directions in which the guide device 16 must be moved in order to achieve axial alignment with the transverse hole in the implanted femoral nail, and making these movements will eventually bring the tube 41 of the drill guide into proper axial alignment, at which point only the central LEDs 91 and 99 will be illuminated. The location on the patient's leg beneath the drill guide is then marked, an incision is made, and retractors are used to keep the incision open. The drill guide is then brought closer and is again positionally adjusted until it is in proper alignment and only the central LEDs 91 and 99 are lit. At this point, the end 42 or the drill guide can be tapped with a hammer in order to drive the teeth into the bone and thus hold at least the lower end of the drill guide in position, but it is not a requirement that the teeth 44 be used in this manner. Then, with the drill guide maintained in position, the drill 17 is used to drill a hole through the bone 12. The switch 109 is then flipped so as to energize the other emitter coil, and then the steps outlined in this paragraph are repeated in association with the other hole 27 (FIG. 1) in the femoral nail.

The conventional and not-illustrated structure which physically interconnects the sleeve 31 to the femoral nail 21 at the proximal end of the femoral nail at the end of the bone is then released, and the sleeve 31 and the coils supported by it are all withdrawn from the femoral nail. Then, self-tapping distal screws are screwed into each of the two screw holes drilled in the bone, each screw passing through a respective one of the transverse holes 26 and 27 (FIG. 1) in the femoral nail in order to securely hold it in place.

As to the alternative embodiment of FIGS. 11 and 12, the sequence described above basically applies. However, before driving the nail assembly 276 into the femur, a nail guide rod 286 is driven into the femur. Then, the nail assembly 276 is coaxially oriented around the exposed end of the rod 186, and is driven into the femur over the rod 286. Then, the rod 286 is extracted.

It will be recognized that a conventional battery backup arrangement could be provided for the RAM 154 of FIG. 5, in order to maintain the data in the RAM even when power to the rest of the system was shut off. Since the zeroing and calibration values obtained by the routines shown in FIG. 10 would thus not be lost when power was turned off, it would not normally be necessary to carry out zeroing and calibration each time the system was turned on.

As to FIGS. 16–20, when either of these alternative embodiments of the emitter coil are used, the system according to the invention operates in the same manner as described above.

Turning to the alternative embodiment of the system shown in FIGS. 21–27, operation is effectively the same as described above. One difference is that, as the drill guide is moved relative to the emitter coil and the signal strengths detected by the respective detector coils increase or decrease, the computer will automatically increase or decrease the gain of the amplifiers 402 (FIG. 23) when the detected signal strength becomes respectively too low or too high. The sequences by which the gain changes are implemented have already been described above in association with FIG. 25. The other difference is that, by adjusting the thumbwheel 393, the operator can control how far either end of the drill guide must deviate from proper axial alignment before one of the arrow-shaped LEDs is illuminated to indicate that a correction is needed. Thus, the operator can adjust the sensitivity and accuracy of the alignment to suit personal preferences and the particular situation presented. The manner in which the computer adjusts the sensitivity based on the thumbwheel setting has already been described above in association with blocks 476 and 481–488 of FIG. 26, and is therefore not described again in detail here.

The two alternative embodiments of the guide device shown in FIGS. 28–30 are used in substantially the same manner as the guide device 16 of FIG. 1, and a detailed discussion of their use is thus not necessary here. It is only necessary to point out that, before use, one of several similar guide tubes 536 is selected for use, the only difference between the several tubes being the axial length of the lower portion 538 thereof. The selection is made so that the axial length of the lower portion 538 corresponds to the depth of tissue or muscle through which the guide must be inserted to reach the bone, a longer axial length being selected for patients with more muscle and tissue, and a shorter axial length for patients with less muscle and tissue.

Although some preferred embodiments have been illustrated and described in detail in order to facilitate an understanding of the present invention, it will be recognized that there are variations or modifications, including the rearrangement of parts, which lie within the scope of the present invention.

The embodiments of the invention in which an exclusive property or privilege is claimed are defined as follows:

1. A medical instrument guide assembly for positioning a medical instrument over a point on a body, said assembly including:

a positioning coil adapted to be inserted in the body so as to be centered along an axis that intersects the point over which the instrument is to be positioned;

a power supply connected to said positioning coil for applying a voltage to said positioning coil so as to cause the generation of a magnetic field centered along an axis intersecting the body point;

an instrument guide for receiving the medical instrument to be positioned, said instrument guide having an elongated center axis;

a first sensor disk attached to said instrument guide so as to be coaxially mounted to said instrument guide at a position proximal to the body, said first sensor disk including a first sensor disk first pair of sensors for monitoring the magnetic field generated around said positioning coil, each said first sensor disk sensor being configured to generate a sensor signal representative of the magnetic field strength in the vicinity of said first sensor disk sensor, said first sensor disk sensors being positioned on said first sensor disk at diametrically opposed locations relative to said instrument guide center axis and being spaced a common distance from said instrument guide center axis;

a second sensor disk attached to said instrument guide so as to be coaxially mounted to said instrument guide at a position distal to the body, said second sensor disk including a second sensor disk first pair of sensors for monitoring the magnetic field generated around said positioning coil, each said second sensor disk sensor being configured to generate a sensor signal representative of the magnetic field strength in the vicinity of said sensor, said second sensor disk sensors being positioned on said second sensor disk at diametrically opposed locations relative to said instrument guide center axis and being spaced a common distance from said instrument guide center axis, wherein said second sensor disk first pair of sensors are spaced further from said instrument guide center axis than the distance at which said first sensor disk first pair of sensors are spaced;

a signal processor connected to said first sensor disk first pair of sensors to receive said sensor signals therefrom and to said second sensor disk first pair of sensors for receiving said sensor signals therefrom, said signal processor being configured to compare said signals produced by said first sensor disk first pair of sensors to each other and to compare said signals produced by said second sensor disk first pair of sensors to each other and, based on said comparisons, to generate sensor disk position signals that indicate if each said sensor disk is centered over the magnetic field axis and, if either said sensor disk is not so positioned, the direction in which said sensor disk should be moved in order to be so positioned; and a display connected to said signal processor for receiving said sensor disk position signals, said display including a plurality of display elements actuatable in response to said sensor disk position signals to indicate if said elongated instrument guide axis is aligned over the body point and if a portion of said instrument guide axis is not so aligned, the direction in which said instrument guide should be moved in order to be so aligned.

2. The medical instrument guide assembly of claim 1, wherein said display is mounted to said instrument guide.

3. The medical instrument guide assembly of claim 1, wherein:

a second pair of sensors is mounted on said first sensor disk for monitoring the magnetic field produced by said positioning coil, said sensors each said first sensor disk sensor pair being located diametrically across from each other relative to said instrument guide center axis and said first sensor disk sensors are mounted on said first sensor disk on a first radius relative to said instrument guide center axis;

a second pair of sensors is mounted on said second sensor disk for monitoring the magnetic field produced by said positioning coil, said sensors of each said second sensor disk sensor pair being located diametrically across from each other relative to said instrument guide center axis and said second sensor disk sensors are mounted on said second sensor disk on a second radius relative to said instrument guide center axis, said second radius on which said second disk sensors are mounted being greater than said first radius on which said first sensor disk sensors are mounted on said first sensor disk; and said signal processor is further configured to produce said sensor disk position signals by comparing said signals from said sensors that form each said pair of sensors.

4. The medical instrument guide assembly of claim 3, wherein said display is mounted to said instrument guide.

5. The medical instrument guide assembly of claim 4, wherein said instrument guide is a hollow tubular member having a center space adapted for receiving the medical instrument.

6. The medical instrument of claim 3, wherein said sensors are coils.

7. The medical instrument guide assembly of claim 3, wherein said instrument guide is a hollow tubular member having a center space adapted for receiving the medical instrument.

8. The medical instrument guide assembly of claim 3, further including an audio generator connected to said signal processor to receive said sensor disk position signals, said audio generator being configured to emit a plurality of audible tones including a distinct tone emitted only when said sensor disk position signals indicate both said sensor disks are aligned with the axis of the magnetic field.

9. The medical instrument of claim 1, wherein said sensors are coils.

10. The medical instrument guide assembly of claim 1, wherein said instrument guide is a hollow tubular member having a center space adapted for receiving the medical instrument.

11. The medical instrument guide assembly of claim 1, further including an audio generator connected to said signal processor to receive said sensor disk position signals, said audio generator being configured to emit a plurality of audible tones including a distinct tone emitted only when said sensor disk position signals indicate both said sensor disks are aligned with the axis of the magnetic field.

12. A positioning system for positioning a cutting instrument over a bore hole formed in an intramedullary nail disposed in a cavity within a bone, the bore hole having an axis, said system including:

a positioning coil configured to be disposed in the intramedullary nail, said coil having a center axis for positioning in the intramedullary nail so as to be axially aligned with the bore hole;

a power supply connected to said positioning coil for applying a voltage to said positioning coil so as to cause the generation of a magnetic field centered along the bore hole axis;

an instrument guide for receiving the cutting instrument to be positioned, said instrument guide having an elongated center axis;

a first sensor disk attached to said instrument guide so as to be coaxially mounted to said instrument guide at a position proximal to the bone, said first sensor disk including a first sensor disk first pair of sensors for monitoring the magnetic field generated around said coil, each said first sensor disk sensor being configured to generate a sensor signal representative of the magnetic field strength in the vicinity of said first sensor disk sensor, said first sensor disk sensors being positioned on said first sensor disk at diametrically opposed locations relative to said instrument guide center axis and being spaced a common distance from said instrument guide center axis;

a second sensor disk attached to said instrument guide so as to be coaxially mounted to said instrument guide at a position distal to the bone, said second sensor disk including a second sensor disk first pair of sensors for monitoring the magnetic field generated around said coil, each said second sensor disk sensor being configured to generate a sensor signal representative of the magnetic field strength in the vicinity of said sensor, said second sensor disk sensors being positioned on said second sensor disk at diametrically opposed locations relative to said instrument guide center axis and being spaced a common distance from said instrument guide center axis, wherein said second sensor disk first pair of sensors are spaced further from said instrument guide center axis than the distance at which said first sensor disk first pair of sensors are spaced; a signal processor connected to said first sensor disk first pair of sensors to receive said sensor signals therefrom and to said second sensor disk first pair of sensors for receiving said sensor signals therefrom, said signal processor being configured to compare said signals produced by said first sensor disk first pair of sensors to each other and to compare said signals produced by said second sensor disk first pair of sensors to each other and, based on said comparisons, to generate sensor disk position signals that indicate if each said sensor disk is centered over the magnetic field axis based on said sensor signals and, if either said sensor disk is not so positioned, the direction which said sensor disk should be moved in order to be so positioned; and a display connected to said signal processor for receiving said sensor disk position signals, said display including a plurality of display elements actuatable in response to said sensor disk position signals to indicate if said elongated instrument guide is aligned over the intramedullary nail bore hole and if a portion of said instrument guide is not so aligned, the direction in which said instrument guide should be moved in order to be so aligned.

13. The positioning system of claim 12, wherein said display is mounted to said instrument guide.

14. The positioning system of claim 12, wherein:

a second pair of sensors is mounted on said first sensor disk for monitoring the magnetic field produced by said coil, said sensors of each said first sensor disk sensor pair being located diametrically across from each other relative to said instrument guide center axis and said first sensor disk sensors are mounted on said first sensor disk on a first radius relative to said instrument guide center axis and;

a second pair of sensors is mounted on said second sensor disk for monitoring the magnetic field produced by said coil, said sensors of each said second disk sensor pair being located diametrically across from each other relative to said instrument guide center axis and said second sensor disk sensors are mounted on said second sensor disk on a second radius relative to said instrument guide center axis, the second radius on which said second disk sensors are mounted being greater than the first radius around which said first sensor disk sensors are mounted on said first sensor disk.

15. The positioning system of claim 14, wherein said display is mounted to said instrument guide.

16. The positioning system of claim 15, wherein said coil is spaced away from the nail bore.

17. The positioning system of claim 14, wherein said sensors are coils.

18. The positioning system of claim 14, wherein said coil is configured to be removably secured in the intramedullary nail.

19. The positioning system of claim 14, further including an audio generator connected to said signal processor to receive said sensor disk position signals, said audio generator being configured to emit a plurality of audible tones including a distinct tone emitted only when said sensor disk position signals indicate both said sensor disks are aligned with the axis of the magnetic field generated by said coil.

20. The positioning system of claim 12, wherein said sensors are coils.

21. The positioning system of claim 12, wherein said coil is configured to be removably secured in the intramedullary nail.

22. The positioning system of claim 12, further including an audio generator connected to said signal processor to receive said sensor disk position signals, said audio generator being configured to emit a plurality of audible tones including a distinct tone emitted only when said sensor disk position signals indicate both said sensor disks are aligned with the axis of the magnetic field generated by said coil.

23. The positioning system of claim 12, wherein said coil comprises a flexible sheet of nonconductive material configured to be removably disposed in the intramedullary nail wherein a conductive trace is located on said flexible sheet so as to function as said coil.

24. The positioning system of claim 12, further including a sleeve configured to be removably disposed in the intramedullary nail wherein said coil is secured to said sleeve.

25. A drill guide for positioning a drill with an elongated drill bit over a point on a bone, said drill guide including:

an elongated guide tube having a center opening for receiving the drill bit, said guide tube having a selected inside diameter and a selected outside diameter;

a positioning assembly configured to locate said guide tube over the selected bone point, said positioning assembly including: a magnetic field generator configured to be positioned in the bone for generating magnetic fields centered on the selected bone point; a sensor array attached to said guide tube for monitoring the strength of the magnetic fields at a plurality of locations spaced from said guide tube, said sensor array being configured to produce sensor signals representative of the monitored magnetic field strength; and a monitoring circuit coupled to receive said sensor signals and including a display assembly, said monitoring circuit being configured to produce an indication on said display assembly when said guide tube is positioned over the selected bone point;

a plurality of tubular locking sleeves, each said tubular locking sleeve having an axially extending center bore for receiving the drill bit and being formed so as to have a stem section shaped with an outside diameter so as to allow said stem section to be disposed in said guide tube and a head section having an outside diameter greater than said inside diameter of said guide tube wherein, said head sections of each said sleeve has a different overall length and one said sleeve is disposed in said guide tube so as to extend outwardly toward the bone.

26. The drill guide of claim 25, wherein said locking sleeve head sections are formed with outwardly extending teeth.

27. The drill guide of claim 25, wherein said locking sleeve head sections are formed to have an outside diameter equal to said outside diameter of said guide tube.

28. The drill guide of claim 25, wherein said positioning assembly sensor array includes first and second sensor disks attached to said guide tube, said first sensor disk being attached to said guide tube at a location proximal to the bone and said second sensor disk being attached to said guide tube at a location distal to said bone; a first sensor disk pair of sensors attached to said first sensor disk for monitoring magnetic field strength; and a second sensor disk pair of sensors attached to said second disk for monitoring magnetic field strength.

29. The drill guide of claim 28, wherein said first sensor disk sensors are mounted to said first sensor disk on a first radius centered around said guide tube center opening and said second disk sensors are mounted to said second sensor disk on a second radius centered around said guide tube center opening, said second radius being greater than said first radius around which said first sensor disk sensors are mounted to said first sensor disk.

* * * * *

UNITED STATES PATENT AND TRADEMARK OFFICE
CERTIFICATE OF CORRECTION

PATENT NO. : 5,584,838
DATED : December 17, 1996
INVENTOR(S) : Mehmet RONA et al It is certified that error appears in the above-indentified patent and that said Letters Patent is hereby corrected as shown below:

Column 27, line 53; change "said sensors each" to ---said sensors of each---.

Column 29, line 6; change "said Second sensor" to ---said second sensor---.

Signed and Sealed this

Tenth Day of June, 1997

*Attest:*

BRUCE LEHMAN

*Attesting Officer*  Commissioner of Patents and Trademarks